(12) United States Patent
Harada et al.

(10) Patent No.: US 10,174,172 B2
(45) Date of Patent: Jan. 8, 2019

(54) JOINED BODY JOINED BY CHEMICAL BONDING AT MATERIAL INTERFACE, AND JOINING METHOD FOR JOINED BODY

(71) Applicant: Osaka University, Suita-shi (JP)

(72) Inventors: Akira Harada, Suita (JP); Hiroyasu Yamaguchi, Suita (JP); Akihito Hashidzume, Suita (JP); Yoshinori Takashima, Suita (JP); Tomoko Sekine, Suita (JP); Yuichiro Kobayashi, Suita (JP); Masaki Nakahata, Suita (JP)

(73) Assignee: Osaka University, Suita-shi (JP)

( * ) Notice: Subject to any disclaimer, the term of this patent is extended or adjusted under 35 U.S.C. 154(b) by 98 days.

(21) Appl. No.: 14/914,455

(22) PCT Filed: Aug. 27, 2014

(86) PCT No.: PCT/JP2014/072488
§ 371 (c)(1),
(2) Date: Jun. 6, 2016

(87) PCT Pub. No.: WO2015/030079
PCT Pub. Date: Mar. 5, 2015

(65) Prior Publication Data
US 2016/0272768 A1 Sep. 22, 2016

(30) Foreign Application Priority Data

Aug. 27, 2013 (JP) .................................. 2013-176128

(51) Int. Cl.
*C08G 81/02* (2006.01)
*C08J 5/12* (2006.01)
*C12N 9/96* (2006.01)
*C09J 5/00* (2006.01)

(52) U.S. Cl.
CPC .............. *C08G 81/021* (2013.01); *C08J 5/12* (2013.01); *C09J 5/00* (2013.01); *C12N 9/96* (2013.01)

(58) Field of Classification Search
CPC ....... C08J 5/12; C09J 5/00; C08L 5/12; C08G 81/021
See application file for complete search history.

(56) References Cited

U.S. PATENT DOCUMENTS

| 2010/0196721 | A1 | 8/2010 | Ogawa |
| 2013/0172479 | A1 | 7/2013 | Harada et al. |
| 2015/0073091 | A1 | 3/2015 | Harada et al. |

FOREIGN PATENT DOCUMENTS

| JP | 58-118237 A | 7/1983 |
| JP | 2006-312278 A | 11/2006 |
| JP | 2008-528508 A | 7/2008 |
| JP | 2011-001481 A | 1/2011 |
| JP | 2013-513135 A | 4/2013 |
| JP | 2013-116130 A | 6/2013 |
| WO | WO-2006/079014 A2 | 7/2006 |
| WO | WO-2008/149745 A1 | 12/2008 |
| WO | WO-2011/071791 A1 | 6/2011 |
| WO | WO-2012/036069 A1 | 3/2012 |
| WO | WO-2013/162019 A1 | 10/2013 |

OTHER PUBLICATIONS

JP 2011-001481 machine translation of original document dated (2011).*
Akira Harada "Self-Healing Supramolecular Material," Polymers, vol. 62, Jul. 2013, p. 371-373 and English abstract thereof.
Akira Harada et al., "Macroscopic self-assembly through molecular recognition," Nature Chemistry, 2011, vol. 3, pp. 34-37.
Akira Harada, "jiko Shufuku Cho Bunshi Material," Kobunshi, 2013, vol. 62, pp. 371-373.
International Search Report dated Nov. 11, 2014, issued for PCT/JP2014/072488.

* cited by examiner

*Primary Examiner* — Edward J Cain
(74) *Attorney, Agent, or Firm* — Locke Lord LLP; James E. Armstrong, IV; Nicholas J. DiCeglie, Jr.

(57) ABSTRACT

The present invention provides a joined body with no risk of detachment from the joining surface without using an adhesive, and a method for producing the joined body. The present invention also provides a reversible joined body that enables control of joining and dissociation, and a method for producing the reversible joined body. In the joined body, a chemical bond is formed between two or more same or different solid-state materials at their contact interfaces by a chemical reaction.

7 Claims, 10 Drawing Sheets
Specification includes a Sequence Listing.

M = Fe : FePor gel
2H : 2HPor gel

JOINED BODY JOINED BY CHEMICAL BONDING AT MATERIAL INTERFACE, AND JOINING METHOD FOR JOINED BODY

TECHNICAL FIELD

The present invention relates to a joined body joined by a chemical bond at material interfaces, and a joining method for the joined body.

BACKGROUND ART

To adhere a plurality of materials, a method of applying an adhesive to the surfaces (joining surfaces) of the materials, and then drying and curing the adhesive has been known. The adhesion principle of this method is mainly mechanical adhesion, physical adhesion, or chemical adhesion.

Mechanical adhesion is an adhesion using anchoring effects. An adhesive applied to a material surface enters into the irregularities of the surfaces and serves as an anchor, thereby adhering the materials.

In physical adhesion, a material surface is wet with an adhesive, thereby adhering the materials by the intermolecular force between the adhesive molecules and the molecules of the material surfaces.

Chemical adhesion is made by a chemical reaction between components in an adhesive and components in the material surfaces.

However, since these adhesion methods use adhesives, they have a drawback of easy detachment of the adhered materials from the joining surfaces. Further, once the materials are adhered, the materials cannot be returned to the state before adhesion; that is, it is impossible to control the adhesion. Additionally, since these adhesion methods require an adhesive, components other than the materials are present between the joining surfaces; thus, the methods have a drawback of possible adverse effects from these components.

CITATION LIST

Patent Documents

Patent Document 1: WO2008/149745

SUMMARY OF INVENTION

Technical Problem

An object of the present invention is to provide a joined body that can be produced without an adhesive and that has no risk of detachment from the joining surfaces; and a method for producing the joined body. Further, another object of the present invention is to provide a reversible joined body that enables control of joining and dissociation; and a method for producing the reversible joined body.

Solution to Problem

The inventors of the present invention conducted extensive research to solve the above problems, and found that by forming a chemical bond between two or more same or different solid-state materials at their contact interfaces by a chemical reaction, it is possible to obtain a joined body with no risk of detachment from the joining surfaces. Further, the inventors also found it possible to obtain a joined body capable of reversible joining, i.e., control between joining and dissociation. The inventors conducted further research based on these findings, and completed the present invention.

More specifically, the present invention provides a joined body, which is joined at material interfaces directly by a chemical bond, and a method for producing the joined body.

Item 1. A joined body wherein two or more same or different solid-state materials are joined directly by a chemical bond at their contact interfaces.

Item 2. The joined body according to Item 1, wherein the chemical bond is a covalent bond.

Item 3. The joined body according to Item 1 or 2, wherein the solid-state materials are at least one kind selected from gels and glass.

Item 4. The joined body according to any one of Items 1 to 3, wherein a solid-state material containing a boronic acid group and a solid-state material containing an aryl halide group are used as the solid-state materials.

Item 5. The joined body according to any one of Items 1 to 3, wherein a solid-state material containing an azide group and a solid-state material containing an ethynyl group are used as the solid-state materials.

Item 6. The joined body according to any one of Items 1 to 3, wherein a solid-state material containing a carboxy group and a solid-state material containing an amino group are used as the solid-state materials.

Item 7. The joined body according to Item 2, wherein the joined body further comprises a noncovalent bond as the chemical bond.

Item 8. The joined body according to Item 1, wherein the chemical bond is a coordinate bond.

Item 9. The joined body according to Item 8, wherein the solid-state materials are gels.

Item 10. The joined body according to Item 8 or 9, wherein a gel containing an apoenzyme and a gel containing a cofactor are used as the solid-state materials.

Item 11. The joined body according to Item 1, wherein the chemical bond is a hydrogen bond.

Item 12. The joined body according to Item 11, wherein the solid-state materials are gels.

Item 13. The joined body according to Item 11 or 12, wherein a gel containing a first nucleic acid base and a gel containing a second nucleic acid base complementary to the first nucleic acid base are used as the solid-state materials.

Item 14. The joined body according to any one of Items 11 to 13, wherein the solid-state material is a gel containing an oligonucleotide.

Item 15. A method for producing a joined body by joining two or more same or different solid-state materials directly by a chemical bond at their contact interfaces.

Item 16. A method for producing a joined body by reacting a solid-state material containing a boronic acid group and a solid-state material containing an aryl halide group at their contact interfaces in the presence of a catalyst.

Item 17. A method for producing a joined body by reacting a solid-state material containing an azide group and a solid-state material containing an ethynyl group at their contact interfaces in the presence of a catalyst.

Item 18. A method for producing a joined body by reacting a solid-state material containing a carboxy group and a solid-state material containing an amino group at their contact interfaces in the presence of a catalyst.

Item 19. A method for producing a joined body by bringing a gel containing an apoenzyme and a gel containing a cofactor into contact with each other.

Item 20. A method for producing a joined body by bringing a gel containing a first nucleic acid base and a gel containing a (second) nucleic acid base complementary to the first nucleic acid base into contact with each other in a solvent.

Advantageous Effects of Invention

The present invention makes it possible to join two or more same or different solid-state materials without using an adhesive.

Because the joined body of the present invention is joined without an adhesive, the joined body has no risk of detachment from the joining surface.

When the chemical bond is a covalent bond, the joined body of the present invention ensures a stable and strong joining.

When the chemical bond is a coordinate bond or a hydrogen bond, the joined body of the present invention is capable of reversible joining and dissociation, and thereby enables control between joining and dissociation as necessary.

DESCRIPTION OF EMBODIMENTS

Figure 1:
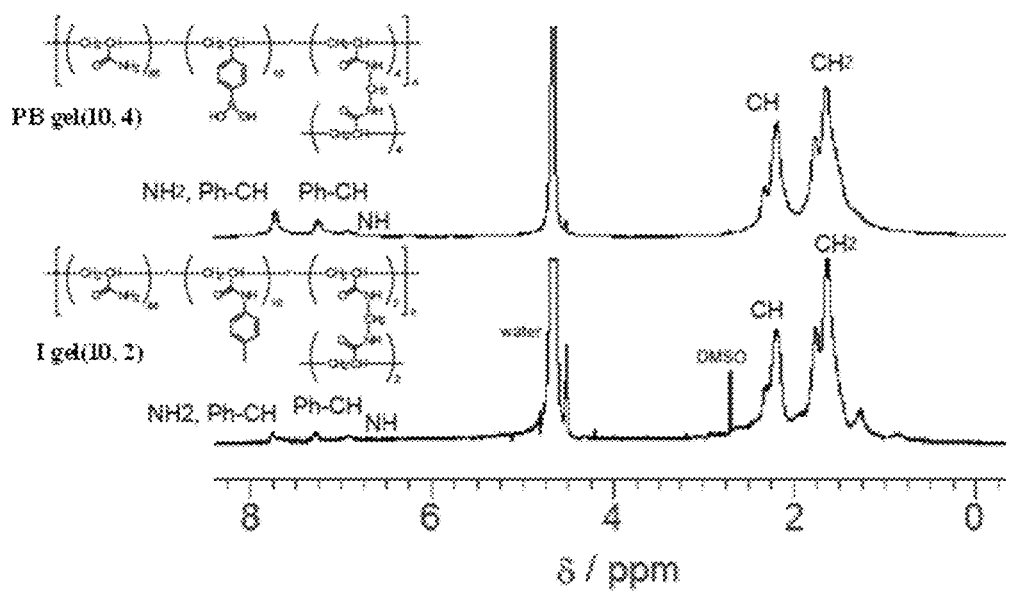
FIG. 1 shows $^1$H-FGMAS NMR data of gels obtained in (1-1) and (1-2) of Example 1.

The present invention is more specifically described below.

The joined body of the present invention is obtained by joining two or more same or different solid-state materials at their contact interfaces directly by a chemical bond.

Solid-state materials include solid materials and semisolid materials. A solid material designates a self-standing material (a state where storage modulus is greater than loss modulus), and a semisolid material designates a material having a storage modulus lower than the loss modulus, and a viscosity of about 1 to 500 Pa·s.

Examples of the solid materials include gels (hydrogel, organogel), glass, wooden plates, plastic, metal plates (gold, iron, palladium, platinum, silver, aluminum, or the like), and paper. Examples of the semisolid materials include slime, high-viscosity polymer solution, clay mineral, and wood putty.

For these solid-state materials, the same kinds or a combination of two or more different kinds may be used.

Examples of the chemical bond include covalent bond, coordinate bond, noncovalent bond (hydrogen bonding, ion-ion interaction, ion-dipole interaction, cation-π interaction, π-π interaction, Van der Waals' force, hydrophobic interaction, host-guest interaction, and the like). The joined body of the present invention may have one kind of chemical bond, or two or more kinds of chemical bond (for example, covalent bond and noncovalent bond (in particular, host-guest interaction)).

The joined body of the present invention may be produced, for example, by introducing a reactive group capable of forming a chemical bond into individual surfaces of two or more solid-state materials, and then reacting the reactive groups.

Various chemical bonds are individually described below in detail.

1. Covalent Bond

When a covalent bond is used as the chemical bond in the joined body of the present invention, the joined body ensures a strong joining and has no risk of detachment from the joining surfaces.

Examples of the covalent bond include a carbon-carbon bond, carbon-nitrogen bond, carbon-oxygen bond, carbon-sulfur bond, sulfur-sulfur bond (disulfide bond), carbon-metal bond, and phosphorus-oxygen bond (phosphodiester bond). The joined body may have only one, or two or more of these bonds.

Specific examples of the carbon-carbon bond include a bond of alkyl group and alkyl group, a bond of aryl group and aryl group, a bond of alkyl group and aryl group, a bond of alkenyl group and aryl group, a bond of carbonyl group having a hydrogen at α-position and aldehyde or ketone group, a bond of α,β-unsaturated carbonyl group and carbanion group, and a bond of phosphorus ylide and carbonyl group.

Specific examples of the carbon-nitrogen bond include an amide bond, imine bond, and triazine ring bond.

Specific examples of the carbon-oxygen bond include an ester bond, ether bond, and ketone bond.

Specific examples of the carbon-sulfur bond include a thioester bond and thioether bond.

Specific examples of the sulfur-sulfur bond include a disulfide bond and the like.

These various covalent bonds are obtained through chemical reactions suitable for the respective bonds.

Examples of chemical reactions for forming a carbon-carbon bond include the Suzuki-Miyaura cross coupling reaction, aldol reaction, Diels-Alder reaction, Grignard reaction, Heck reaction, Michael addition reaction, Wittig reaction, ring-closing metathesis reaction, and photocyclization reaction.

Examples of chemical reactions for forming a carbon-nitrogen bond include a substitution reaction of carboxylic acid (ester) and amine (amide bond-forming reaction), and cycloaddition reaction (azide alkyne cycloaddition) in which alkine and an azide compound undergo a cycloaddition reaction, thereby forming a 1,2,3-triazole ring.

Examples of chemical reactions for forming a carbon-oxygen bond include a dehydration reaction of carboxylic acid and alcohol (ester bond-forming reaction), Williamson synthesis, and ether synthesis through an electrophilic addition reaction in which an electrophile is caused to act on olefin in the presence of an alcohol.

Examples of chemical reactions for forming a carbon-sulfur bond include a dehydration reaction of carboxylic acid and thiol (thioester bond-forming reaction), and the like.

Examples of chemical reactions for forming a sulfur-sulfur bond include a coupling reaction of thiol and the like.

Examples of chemical reactions for forming a carbon-metal bond include a ring-closing metathesis reaction, coordination polymerization, and oxidative addition reaction.

Examples of chemical reactions for forming a phosphorus-oxygen bond include an esterification reaction and Perkow reaction.

When the chemical bond is a covalent bond, any of the solid-state materials listed above, i.e., gels (hydrogel, organogel), glass, wooden plates, plastic, metal plates (gold, iron, palladium, platinum, silver, aluminum, or the like), and paper, may be used. However, gels and glass are particularly preferable. It is also possible to use a gel and glass together. More specifically, it is possible to join a gel and a gel, or glass and glass by a chemical bond, or join a gel and glass by a chemical bond.

Examples of the gels include a gel having repeating units represented by Formula (1) below, and a crosslinking agent.

[Chem. 1]

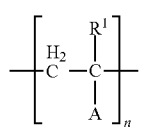

(1)

wherein $R^1$ represents a hydrogen atom or a methyl group; A represents an optionally substituted aryl group, $C(O)OR^a$, or $C(O)NHR^a$; $R^a$ represents a hydrogen atom, an optionally substituted alkyl group, an optionally substituted aryl group, or an optionally substituted arylalkyl group; and n is 100 to 10,000,000.

When a gel having the repeating units represented by Formula (1) is used, the joined body may be produced, for example, by introducing a reactive group capable of forming a covalent bond into each gel, and then reacting the reactive groups.

Formation of a carbon-carbon bond is described below as an example.

1-1. Carbon-Carbon Bond

When a carbon-carbon bond is formed as a covalent bond, the joined body of the present invention may be produced, for example, by introducing a boronic acid group into one of the gels to be joined while introducing an aryl halide group into the other gel, and performing the Suzuki-Miyaura coupling reaction.

1-1-1. Boronic Acid Group-Containing Gel

A gel in which a boronic acid group is introduced is expressed, for example, by Formula (2) below.

[Chem. 2]

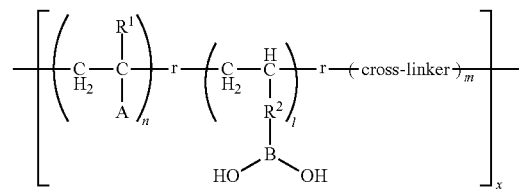

(2)

wherein $R^1$ is the same or different, and each represents a hydrogen atom or a methyl group; $R^2$ represents an alkylene group or an arylene group; A represents an optionally substituted aryl group, $C(O)OR^a$, or $C(O)NHR^a$; $R^a$ represents a hydrogen atom, an optionally substituted alkyl group, an optionally substituted aryl group, or an optionally substituted arylalkyl group; "cross-linker" represents a bi- to tetra-functional crosslinking agent; n+m+1=100 mol % wherein n is 0 to 99.8, m is 0.1 to 99.9, and 1 is 0.1 to 99.9; x is 2 to 10,000,000; and -r- represents a random bond in which individual repeating units are aligned at random, thereby forming a so-called random polymer. The same is applied to the formulas below.

For the gel represented by Formula (3) above, the ratio n:l:m is preferably 1:0.1:98.9 to 99.8:0.1:0.1 (mol % ratio). Particularly preferably, the ratio n:l:m is 94:2:2 to 76:20:2 (mol % ratio).

A gel having a boronic acid group represented by Formula (2) above may be produced, for example, by reacting compounds represented by Formulas (3) and (4) below, and a compound represented by a bi- to tetra-functional crosslinking agent.

[Chem. 3]

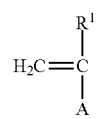

(3)

wherein $R^1$ represents a hydrogen atom or a methyl group; A represents an optionally substituted aryl group, $C(O)OR^a$, or $C(O)NHR^a$; and $R^a$ represents a hydrogen atom, an optionally substituted alkyl group, an optionally substituted aryl group, or an optionally substituted arylalkyl group.

[Chem. 4]

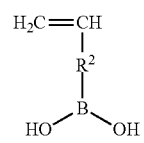

(4)

wherein $R^2$ represents an alkylene group or an arylene group.

In Formula (3) above, examples of the alkyl group of the optionally substituted alkyl group represented by $R^a$ include linear, branched, or cyclic C1-18 alkyl groups. Specific examples include methyl, ethyl, n-propyl, isopropyl, n-butyl, isobutyl, sec-butyl, tert-butyl, pentyl, cyclopentyl, hexyl, cyclohexyl, isohexyl, dodecyl, octadecyl, and adamantyl. Of these, hydrogen group and methyl group are preferable, and hydrogen group is particularly preferable. The alkyl group may have 1 to 3 substituents, such as halogen atom (e.g., fluorine, chlorine, bromine, etc.), carboxyl group, ester group, amide group, and protected or unprotected hydroxy group. The alkyl group may be an alkyl group to which ferrocene, which is an organic metal complex, is bonded as a substituent.

Examples of the aryl group of the optionally substituted aryl group represented by A and $R^a$ in Formula (3) above include monocyclic or polycyclic aryl groups. Specific examples include phenyl, toluyl, xylyl, naphthyl, anthryl, and phenanthryl. Of these, phenyl group is preferable. The aryl group may have 1 to 3 substituents, such as alkyl group (e.g., C1-18 alkyl group etc.), halogen atom (e.g., fluorine, chlorine, bromine, etc.), carboxyl group, ester group, amide group, azo group having aryl group, or protected or unprotected hydroxy group.

In Formula (3) above, examples of the arylalkyl group of the optionally substituted arylalkyl group represented by $R^a$ include linear or branched C1-3 lower alkyl substituted with the monocyclic or polycyclic aryl group mentioned above. Specific examples include benzyl group, naphthyl methyl group, anthracene methyl group, and pyrene methyl group. Of these, benzyl group and naphthyl methyl group are preferable. The aryl group may have 1 to 3 substituents, such as alkyl group (e.g., C1-18 alkyl group, etc.), halogen atom (e.g., fluorine, chlorine, bromine, etc.), carboxyl group, ester group, amide group, azo group having aryl group, and protected or unprotected hydroxy group. Examples include hydroxy phenyl methyl group, methyl phenyl methyl group, dimethyl phenyl methyl group, trimethyl phenyl methyl group, carboxyphenyl methyl group, hydroxy methyl phenyl methyl group, and triphenylmethyl group.

Preferable examples of the compound represented by Formula (3) include acrylamide, n-butyl acrylate, t-butyl acrylate, N-(1-adamantyl)acrylamide, N-benzylacrylamide, N-1-naphthylmethylacrylamide, styrene, acrylic acid, ethyl acrylate, butyl acrylate, hexyl acrylate, lauryl acrylate, octadecyl acrylate, t-butyl acrylate, isobutyl acrylate, 2-hydroxyethyl acrylate, hydroxypropyl acrylate, 4-hydroxybutyl acrylate, 2-carboxyethyl acrylate, di(ethyleneglycol) ethylether acrylate, di(ethyleneglycol)2-ethylhexylether acrylate, poly(propyleneglycol)acrylate, poly(ethyleneglycol)methylethyl acrylate, N,N-dimethyl acrylamide, N-isopropylacrylamide, N-tert-butyl acrylamide, N-hydroxymethyl acrylamide, N-hydroxyethyl acrylamide, N-[tris(hydroxymethyl)methyl]acrylamide, N-(3-methoxypropyl) acrylamide, glycidyl methacrylate, methacrylic acid N-hydroxysuccinimide ester, triethyleneglycol methylester methacrylate, methacrylic acid, methyl methacrylate, ethyl methacrylate, 2,2,2-trifluoroethyl methacrylate, butyl methacrylate, 2-hydroxyethyl methacrylate, 2-hydroxyethyl methacrylate, hydroxypropyl methacrylate, 2-aminoethyl methacrylate hydrochloride, and 2-(dimethylamino) ethyl methacrylate.

Among the compound represented by Formula (3) above, only one kind, or two or more kinds may be used.

When A in the compound represented by Formula (3) above is an optionally substituted aryl group, a commercially available monomer (such as styrene) may be used as is.

When A in the compound represented by Formula (3) above is $C(O)OR^a$ or $C(O)NHR^a$, the compound is produced by reacting an amino compound of alkyl or aryl as the substituent represented by $R^a$ with acrylic acid chloride. Generally, acrylic acid chloride and an amino compound of alkyl or aryl as the substituent represented by $R^a$ are mixed in a solvent, followed by stirring.

The reaction may be performed without a solvent, or with a solvent (organic solvent or aqueous solvent) generally used for organic synthesis reactions. Examples of the organic solvent include dimethyl sulfoxide (DMSO), dimethylformamide (DMF), and the like. Examples of the aqueous solvent include water, and buffers containing a salt such as sodium phosphate or sodium carbonate as necessary. When a solvent is used, the amount of the solvent is suitably adjusted.

Further, when A in the compound represented by Formula (3) is $C(O)NHR^8$, the compound may be produced by adding 1,1'-carbonyldiimidazole (CDI) or 1-ethyl-3-(3-dimethylaminopropyl)carbodiimide hydrochloride (EDC) to acrylic acid under ice-cooling, and then adding amino cyclodextrin thereto, followed by stirring overnight, thereby forming an amide bond; or by adding dicyclohexylcarbodiimide (DCC), and 1-hydroxy benzotriazole (HOBt) or N-hydroxysuccinimide (HOSu) as a condensing agent to acrylic acid, thereby producing an amide compound via an active ester.

Further, when A in the compound represented by Formula (3) is $C(O)OR^a$, the compound may be produced by adding N,N-dimethyl-4-aminopyridine to acrylic acid under ice-cooling, and then adding cyclodextrin thereto, followed by stirring overnight, thereby forming an ester bond; or by adding dicyclohexylcarbodiimide (DCC), and 1-hydroxy benzotriazole (HOBt) or N-hydroxysuccinimide (HOSu) as a condensing agent to acrylic acid, thereby producing an ester compound via an active ester.

Examples of the alkylene group represented by $R^2$ in Formula (4) include ethylene group, methylene group, propylene group, butylene group, pentyl group, hexyl group, heptyl group, octyl group, nonenyl group, and decanyl group. Of these, ethylene group is preferable.

The arylene group represented by $R^2$ in Formula (4) includes phenylene group, tolylene group, xylylene group, and durylene group.

Preferable examples of the compound represented by Formula (4) include 4-vinylphenyl boronic acid, diisopropyl acrylic boronate, and dibutyl vinyl boronate. In particular, 4-vinylphenyl boronic acid is preferable.

Known compounds may be used as the compounds represented by Formula (4). Further, only one kind or two or more kinds of the compound represented by Formula (4) above may be used.

Examples of bi- to tetra-functional crosslinking agent include N,N'-methylene-bis-acrylamide, divinylbenzene, ethyleneglycol diacrylate, di(ethyleneglycol)diacrylate, tetra(ethyleneglycol)diacrylate, poly(ethyleneglycol)diacrylate, 1,4-butanediol diacrylate, 1,6-hexanediol diacrylate, tri(propyleneglycol)diacrylate, trimethylolpropane triacrylate, pentaerythritol triacrylate, pentaerythritol tetraacrylate, bis(2-methacryloyl)oxyethyl disulfide, 1,4-butanediol dimethacrylate, 1,6-hexanediol dimethacrylate, ethyleneglycol diacrylamide, di(ethyleneglycol)diacrylamide, tetra(ethyleneglycol)diacrylamide, poly(ethyleneglycol)diacrylamide, 1,4-butanediol diacrylamide, 1,6-hexanediol diacrylamide, tri(propyleneglycol)diacrylamide, trimethylolpropane triacrylamide, pentaerythritol triacrylamide, pentaerythritol tetraacrylamide, bis(2-methacryloyl)oxyethyl disulfide, 1,4-butanediol dimethacrylamide, and 1,6-hexanediol dimethacrylamide. Of these, N,N'-methylene-bis-acrylamide and divinylbenzene are preferable.

Known agents may be used as the bi- to tetra-functional crosslinking agents listed above. Further, only one kind of functional crosslinking agent, or two or more kinds of functional crosslinking agent may be used.

The gel in which boronic acid group is introduced represented by Formula (2) above is produced by subjecting the compounds represented by Formulas (3) and (4) and the above bi- to tetra-functional crosslinking agent to radical polymerization. Generally, the compounds represented by Formulas (3) and (4), the bi- to tetra-functional crosslinking agent, and, if necessary, a radical polymerization initiator are mixed and stirred in a container substituted with inert gas, or a vacuum-deaerated container.

The radical polymerization reaction may be performed without a solvent, or with a solvent (organic solvent or aqueous solvent) generally used for radical polymerization. Examples of the organic solvent include benzene, toluene, N,N-dimethylformamide (DMF), dimethyl sulfoxide (DMSO), acetone, chloroform, carbon tetrachloride, tetrahydrofuran (THF), ethyl acetate, chlorobenzene, dichlorobenzene, trifluoro methylbenzene, and anisole. Examples of the aqueous solvent include water, and solvents including, as necessary, methanol, ethanol, isopropanol, n-butanol, ethyl cellosolve, butyl cellosolve, and 1-methoxy-2-propanol.

When a solvent is used, the amount of the solvent may be suitably adjusted; however, the amount of the solvent is, for example, generally 0.1 to 1 liter, preferably 0.2 to 0.5 liter, per mol of the total monomer used for the polymerization.

The radical polymerization reaction may be performed in the presence or absence of a radical polymerization initiator. Generally, the radical polymerization reaction is preferably performed in the presence of a radical polymerization initiator. It is also possible to perform radical polymerization as natural heat polymerization in the absence of a radical polymerization initiator, or perform radical polymerization with optical irradiation in the presence or absence of a radical polymerization initiator. In the case of radical polymerization with optical irradiation, polymerization is generally performed using a light source such as a mercury lamp, xenon lamp, or the like. The light source may be suitably selected depending on the type of the compound used for the reaction, the type of the polymerization initiator, and the like.

This reaction may generally be performed in a range of about −20° C. to 150° C., preferably in a range of about 20 to 80° C. The reaction time varies depending on the type of the reaction reagent, the reaction temperature, and the like, and thus cannot be unconditionally stated; however, the reaction is generally completed in about 1 to 48 hours.

1-1-2. Halogenated Aryl Group-Containing Gel

The gel in which aryl halide group is introduced is, for example, represented by Formula (5) below. Formula (5) below is a chemical formula showing an example of a gel in which aryl halide group is introduced wherein the halogen is iodine.

[Chem. 5]

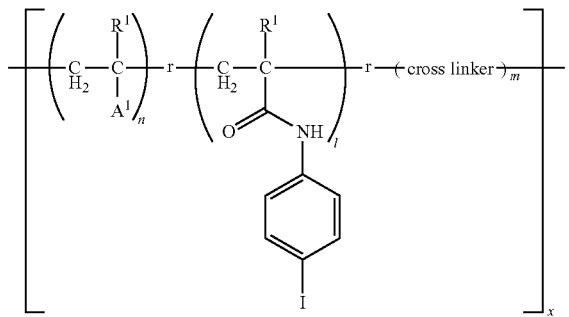

(5)

wherein $R^1$ is the same or different, and each represents a hydrogen atom or a methyl group; $A^1$ represents an optionally substituted aryl group, $C(O)NHR^a$, or $C(O)OR^b$; $R^a$ represents a hydrogen atom, an optionally substituted alkyl group, an optionally substituted aryl group, or an optionally substituted arylalkyl group; $R^b$ represents an optionally substituted alkyl group, an optionally substituted aryl group, or an optionally substituted arylalkyl group; "cross-linker" represents a bi- to tetra-functional crosslinking agent; n+m+1=100 mol % wherein n is 0 to 99.8, m is 0.1 to 99.9, and 1 is 0.1 to 99.9; x is 2 to 10,000,000; and -r- represents a random bond.

In the gel represented by Formula (5) above, the ratio n:l:m is preferably 1:0.1:98.9 to 99.8:0.1:0.1 (mol % ratio). Particularly preferably, the ratio n:l:m is 96:2:2 to 78:20:2 (mol % ratio).

The aryl halide group-containing gel represented by Formula (5) above may be produced, for example, by reacting the compounds represented by Formulas (6) and (7) below, and the bi- to tetra-functional crosslinking agent, and then leading the aryl halide group to the carboxy group derived from the compound represented by Formula (7).

[Chem. 6]

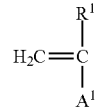

(6)

wherein $R^1$ represents a hydrogen atom or a methyl group; $A^1$ represents an optionally substituted aryl group, $C(O)NHR^a$, or $C(O)OR^b$; $R^a$ represents a hydrogen atom, an optionally substituted alkyl group, an optionally substituted aryl group, or an optionally substituted arylalkyl group; and $R^b$ represents an optionally substituted alkyl group, an optionally substituted aryl group, or an optionally substituted arylalkyl group.

[Chem. 7]

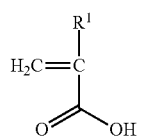

(7)

wherein R¹ represents a hydrogen atom or a methyl group.

In Formula (6) above, examples of the optionally substituted alkyl group, optionally substituted aryl group, and optionally substituted arylalkyl group represented by $R^a$ include groups similar to those in Formula (3) above.

Further, in Formula (6) above, examples of the optionally substituted aryl group represented by $A^1$ include groups similar to those in Formula (3) above.

Preferable examples of the compound represented by Formula (6) above include acrylamide, n-butyl acrylate, t-butyl acrylate, N-(1-adamantyl)acrylamide, N-benzylacrylamide, N-1-naphthylmethylacrylamide, styrene, ethyl acrylate, butyl acrylate, hexyl acrylate, lauryl acrylate, octadecyl acrylate, t-butyl acrylate, isobutyl acrylate, 2-hydroxyethyl acrylate, hydroxypropyl acrylate, 4-hydroxybutyl acrylate, 2-carboxyethyl acrylate, di(ethyleneglycol) ethylether acrylate, di(ethyleneglycol)2-ethylhexylether acrylate, poly(propyleneglycol)acrylate, poly(ethyleneglycol)methylethyl acrylate, N,N-dimethyl acrylamide, N-isopropylacrylamide, N-tert-butyl acrylamide, N-hydroxymethyl acrylamide, N-hydroxyethyl acrylamide, N-[tris(hydroxymethyl) methyl]acrylamide, N-(3-methoxypropyl)acrylamide, glycidyl methacrylate, methacrylic acid N-hydroxysuccinimide ester, triethyleneglycol methylester methacrylate, methyl methacrylate, ethyl methacrylate, 2,2,2-trifluoroethyl methacrylate, butyl methacrylate, 2-hydroxyethyl methacrylate, 2-hydroxyethyl methacrylate, hydroxypropyl methacrylate, 2-aminoethyl methacrylate hydrochloride, and 2-(dimethylamino)ethyl methacrylate.

Further, only one kind of the compound represented by Formula (6) above, or two or more kinds of the compound represented by Formula (6) may be used.

Known compounds may be used as the compounds represented by Formula (7) above. Further, only one kind or two or more kinds of the compound represented by Formula (7) above may be used. In particular, acrylic acid is preferable.

The method of reacting the compounds represented by Formulas (6) and (7) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

Subsequently, a halogen compound having an amino group is reacted with the carboxy group derived from the compound represented by Formula (7) above, thereby obtaining an aryl halide group-containing gel represented by Formula (5) above.

Examples of the halogen compound having an amino group include the compound represented by Formula (8) below.

[Chem. 8]

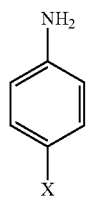

(8)

wherein X represents a halogen atom.

Examples of the halogen atom include iodine, bromine, and chlorine. Iodine is preferable.

The gel containing a halogen compound represented by Formula (5) above is generally obtained by mixing a polymer obtained by reacting the compounds represented by Formulas (6) and (7) above and the bi- to tetra-functional crosslinking agent; the halogen compound containing an amino group represented by Formula (8) above; a condensing agent; and, as necessary, a tertiary amine compound in a solvent, and then shaking the mixture.

As the solvent, a solvent capable of swelling the polymer obtained by reacting the compounds represented by Formulas (6) and (7) above and the bi- to tetra-functional crosslinking agent, and a solvent generally used for condensation reaction may be used. Examples of the solvent include dimethyl sulfoxide (DMSO), aqueous solvents, and the like.

Examples of condensing agent include benzotriazol-1-yloxy-trisdimethylamino phosphonium salt (Bop reagent), diphenylphosphoryl azide (DPPA), 4-(4,6-dimethoxy-1,3,5-triazin-2-yl)-4-methylmorpholinium chloride (DMT-MM), (benzotriazol-1-yloxy)trispyrrolidinophosphonium hexafluorophosphate (PyBOP), and 1-ethyl-3-(3-dimethylaminopropyl)carbodiimide hydrochloride (EDC).

Further, as necessary, a tertiary amine compound may also be used. Specific examples of tertiary amine compound include triethylamine, and pyridine.

This reaction may generally be performed in a range of about 0° C. to 80° C., preferably in a range of about 20 to 40° C. The reaction time varies depending on the type of the reaction reagent, the reaction temperature, and the like, and thus cannot be unconditionally stated; however, the reaction is generally completed in about 1 to 24 hours.

1-1-3. Joining (Suzuki-Miyaura Coupling Reaction)

By performing the Suzuki-Miyaura coupling reaction in the contact interfaces of the gels obtained in 1-1-1 and 1-1-2 above, it is possible to obtain the joined body of the present invention.

The Suzuki-Miyaura coupling reaction is performed by bringing the interfaces of the gels obtained in 1-1-1 and 1-1-2 above into contact with each other in the presence of a nucleophilic agent and a palladium catalyst. This reaction may be performed without a solvent, or in the presence of a solvent.

Any generally used solvents (organic solvent or aqueous solvent) may be used. Examples of the organic solvent include toluene, tetrahydrofuran, acetone, acetonitrile, DMSO, and DMF. Examples of the aqueous solvent include water; and solvents including, as necessary, methanol, ethanol, isopropanol and the like. Water is preferable.

Examples of the nucleophilic agent include potassium carbonate, sodium carbonate, potassium phosphate, and like salts, and amine. Potassium carbonate is preferable.

Examples of the palladium catalyst include palladium acetate and tetrakis(triphenylphosphine) palladium. Palladium acetate is preferable.

This reaction may generally be performed in a range from room temperature (about 15° C.) to about 90° C., preferably in a range of about 20 to 40° C. The reaction time varies depending on the type of the reaction reagent, the reaction temperature, and the like, and thus cannot be unconditionally stated; however, the reaction is generally completed in about 2 to 24 hours.

1-1-4. Boronic Acid Group-Containing Glass Substrate

A glass substrate may also be used as the solid-state material. A glass substrate containing a boronic acid group may be obtained, for example, by first ozone-treating a glass substrate, reacting a silane coupling agent having an amino group with the ozone-treated surface of the glass substrate, thereby introducing the amino group, and causing condensation of the amino group and the boronic acid having a carboxyl group.

The ozone treatment is not particularly limited, and known methods may be used. For example, the ozone treatment may be performed using an ozone cleaner (UV253 Filgen, Inc.).

Examples of the silane coupling agent having an amino group include 3-aminopropyltriethoxysilane, 3-aminopropyltrimethoxysilane, diethoxy(3-glycidyloxypropyl)methylsilane, 3-glycidyloxypropyl trimethoxysilane, 3-glycidyloxypropyl(dimethoxy)methylsilane, 3-(2-aminoethylamino)propyltriethoxysilane, 3-aminopropyltrimethoxysilane, and 3-aminopropyldiethoxymethylsilane. 3-aminopropyltriethoxysilane is preferable.

Examples of the boronic acid having a carboxyl group include 5-carboxy-2-fluorophenylboronic acid, 4-carboxy-3-fluorophenylboronic acid, 3-carboxy-4-fluorophenylboronic acid, 4-carboxy-3-chlorophenylboronic acid, 4-carboxy-2-nitrophenylboronic acid, 3-carboxy-5-nitrophenylboronic acid, p-chlorocarbonylphenylboronic acid, o-carboxyphenylboronic acid, m-carboxyphenylboronic acid, m-carboxyphenylboronic acid, 3-(4,4,5,5-tetramethyl-1,3,2-dioxaborolan-2-yl)benzoic acid, 4-(4,4,5,5-tetramethyl-1,3,2-dioxaborolan-2-yl)benzoic acid, and 3-nitro-5-(4,4,5,5-tetramethyl-1,3,2-dioxaborolan-2-yl)benzoic acid.

By reacting the silane coupling agent having an amino group in air at room temperature or under heating (15 to 80° C.), an amino group is introduced into the surface of the glass substrate.

The reaction to cause condensation of the boronic acid having a carboxyl group with the glass substrate having an amino group on the surface is similar to the reaction of producing the compound represented by Formula (5) above by reacting a polymer obtained by reacting the compounds represented by Formulas (6) and (7) above and the bi- to tetra-functional crosslinking agent; a halogen compound having an amino group; a condensing agent; and, as necessary, a tertiary amine compound.

1-1-5. Halogenated Aryl Group-Containing Glass Substrate

A glass substrate containing an aryl halide group may also be used as the solid-state material. The glass substrate containing an aryl halide group may be obtained, for example, by first ozone-treating a glass substrate, reacting a silane coupling agent having an amino group with the ozone-treated surface of the glass substrate, thereby introducing the amino group, and causing condensation of the amino group and a halogen compound having a carboxyl group.

The ozone treatment is similar to that described in 1-1-4 above.

Examples of the silane coupling agent having an amino group include those described in 1-1-4 above.

Examples of halogen compound having a carboxyl group include 5-carboxy-2-fluoro-iodobenzene, 4-carboxy-3-fluoroiodobenzene, 3-carboxy-4-fluoroiodobenzene, 4-carboxy-3-chloroiodobenzene, 4-carboxy-2-nitroiodobenzene, 3-carboxy-5-nitroiodobenzene, p-chlorocarbonyl iodobenzene, o-carboxyiodobenzene, m-carboxyiodobenzene, and p-carboxyiodobenzene.

The reaction of reacting a silane coupling agent having an amino group with the ozone-treated surface of the ozone-treated glass substrate, thereby introduce an amino group, and the reaction of causing condensation of the amino group and a halogen compound having a carboxyl group are similar to those described in 1-1-4 above.

1-1-6. Joining (Suzuki-Miyaura Coupling Reaction Between Glass Substrate and Gel)

By performing the Suzuki-Miyaura coupling reaction in the contact interfaces of the gel obtained in 1-1-1 above and the glass substrate obtained in 1-1-5, and the contact interfaces of the gel obtained in 1-1-2 above and the glass substrate obtained in 1-1-4, it is possible to obtain the joined body of the present invention.

The Suzuki-Miyaura coupling reaction is performed by bringing the gel obtained in 1-1-1 above and the glass substrate obtained in 1-1-5 into contact with each other, or bringing the gel obtained in 1-1-2 above and the glass substrate obtained in 1-1-4 into contact with each other, in the presence of a nucleophilic agent and a palladium catalyst. The conditions in this reaction are similar to those in the reaction described in 1-1-3 above.

1-2. Carbon-Nitrogen Bond

Further, when a carbon-nitrogen bond is formed as a covalent bond, it is possible to introduce an azide group into one of the gels to be joined, and introduce an ethynyl group into the other gel so as to perform an azide-alkyne cycloaddition reaction, thereby producing a joined body.

A joined body having a carbon-nitrogen bond as a covalent bond may also be produced by introducing a carboxy group into one of the gels to be joined and introducing an amino group into the other gel, thereby performing an amidation reaction. Further, the joined body may also have a joining by a noncovalent bond (for example, host-guest interaction), in addition to the covalent bond. By having two or more kinds of chemical bond, the joining may selectively be made. Further, it is also possible to obtain a high-strength joining in a shorter period of time.

1-2-1. Azide Group-Containing Gel

The gel in which an azide group is introduced is represented, for example, by Formula (9) below.

[Chem. 9]

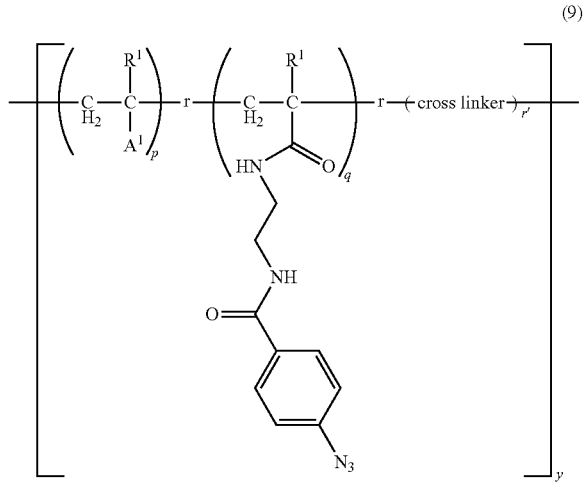

(9)

wherein $R^1$ is the same or different, and each represents a hydrogen atom or a methyl group; $A^1$ represents an optionally substituted aryl group, $C(O)NHR^a$, or $C(O)OR^b$; $R^a$ represents a hydrogen atom, an optionally substituted alkyl group, an optionally substituted aryl group, or an optionally substituted arylalkyl group; $R^b$ represents an optionally substituted alkyl group, an optionally substituted aryl group, or an optionally substituted arylalkyl group; "cross-linker" represents a bi- to tetra-functional crosslinking agent; p+q+r'=100 mol % wherein p is 0 to 99.8, q is 0.1 to 99.9, and r' is 0.1 to 99.9; y is 2 to 10,000,000; and -r- represents a random bond.

In the gel represented by Formula (9) above, the ratio p:q:r' is preferably 1:0.1:98.9 to 99.8:0.1:0.1 (mol % ratio). Particularly preferably, the ratio p:q:r' is 76:2:2 to 78:20:2 (mol % ratio).

The gel having an azide group represented by Formula (9) above may be produced, for example, by reacting the compounds represented by Formulas (6) and (7) above and the bi- to tetra-functional crosslinking agent, and then leading the azide group to the carboxy group derived from the compound represented by Formula (7).

The method of reacting the compounds represented by Formulas (6) and (7) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

Subsequently, the carboxy group derived from the compound represented by Formula (7) above is reacted with an azide compound having an amino group, thereby obtaining the gel containing an azide group represented by Formula (9) above.

Examples of the azide compound having an amino group include the compound represented by Formula (10) below.

[Chem. 10]

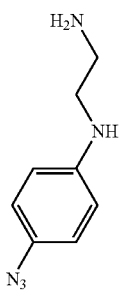

(10)

The gel containing an azide group represented by Formula (9) above is generally obtained by mixing a polymer obtained by reacting the compounds represented by Formulas (6) and (7) above and the bi- to tetra-functional crosslinking agent; the azide compound having an amino group represented by Formula (10) above; a condensing agent; and, as necessary, a tertiary amine compound in a solvent, and then shaking the mixture. The conditions in the above reaction are similar to those in the reaction of producing the gel represented by Formula (5) above by reacting a polymer obtained by reacting the compounds represented by Formulas (6) and (7) above and the bi- to tetra-functional crosslinking agent; the halogen compound containing an amino group represented by Formula (8) above; a condensing agent; and, as necessary, a tertiary amine compound.

1-2-2. Ethynyl Group-Containing Gel

The gel in which an ethynyl group is introduced is represented, for example, by Formula (11) below.

[Chem. 11]

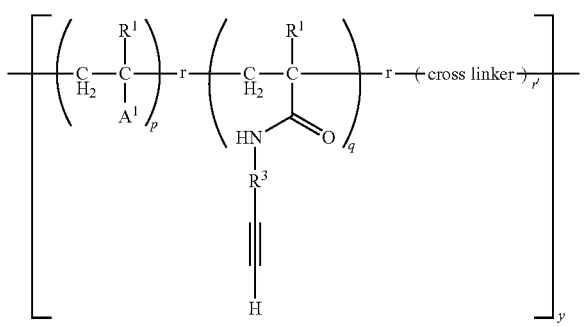

(11)

wherein $R^1$ is the same or different, and each represents a hydrogen atom or a methyl group; $R^3$ represents an alkylene group or an arylene group; $A^1$ represents an optionally substituted aryl group, $C(O)NHR^a$, or $C(O)OR^b$; $R^a$ represents a hydrogen atom, an optionally substituted alkyl group, an optionally substituted aryl group, or an optionally substituted arylalkyl group; $R^b$ represents an optionally substituted alkyl group, an optionally substituted aryl group, or an optionally substituted arylalkyl group; "cross-linker" represents a bi- to tetra-functional crosslinking agent; p+q+r'=100 mol % wherein p is 0 to 99.8, q is 0.1 to 99.9, and r' is 0.1 to 99.9; y is 2 to 10,000,000; and -r- represents a random bond.

In the gel represented by Formula (11) above, the ratio p:q:r' is preferably 1:0.1:98.9 to 99.8:0.1:0.1 (mol % ratio). Particularly preferably, the ratio p:q:r' is 76:2:2 to 78:20:2 (mol % ratio).

The gel having an ethynyl group represented by Formula (11) above may be produced, for example, by reacting the compounds represented by Formulas (6) and (7) above and the bi- to tetra-functional crosslinking agent, and then leading the ethynyl group to the carboxy group derived from the compound represented by Formula (7).

The method of reacting the compounds represented by Formulas (6) and (7) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

Subsequently, the carboxy group derived from the compound represented by Formula (7) is reacted with an ethynyl compound, thereby obtaining a gel containing an ethynyl group.

Examples of ethynyl compound include the compound represented by Formula (12) below.

[Chem. 12]

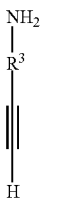
(12)

wherein $R^3$ represents an alkylene group or an arylene group.

In Formula (12) above, examples of the alkylene group represented by $R^3$ include ethylene group, methylene group, propylene group, butylene group, pentyl group, hexyl group, heptyl group, octyl group, nonenyl group, and decanyl group. Ethylene group is preferable.

In Formula (12) above, examples of the arylene group represented by $R^3$ include phenylene group, biphenyl group, dimethyl phenylene group, and diethyl phenylene group. Phenylene group is preferable.

The gel containing an ethynyl group represented by Formula (11) above is generally obtained by mixing a polymer obtained by reacting the compounds represented by Formulas (6) and (7) above and the bi- to tetra-functional crosslinking agent; the ethynyl compound represented by Formula (12) above; a condensing agent; and, as necessary, a tertiary amine compound in a solvent, and then shaking the mixture.

The conditions in the above reaction are similar to those in the reaction of producing the compound represented by Formula (5) above by reacting a polymer obtained by reacting the compounds represented by Formulas (6) and (7) above and the bi- to tetra-functional crosslinking agent; the halogen compound containing an amino group represented by Formula (8) above; a condensing agent; and, as necessary, a tertiary amine compound.

1-2-3. Joining (Azide-Alkyne Cycloaddition Reaction)

By performing an azide-alkyne cycloaddition reaction in the contact interfaces of the gels obtained in 1-2-1 and 1-2-2 above, it is possible to obtain the joined body of the present invention.

The azide-alkyne cycloaddition reaction is performed by bringing the interfaces of the gels obtained in 1-2-1 and 1-2-2 above into contact with each other in the presence of a copper catalyst and a reducing agent. This reaction may be performed without a solvent, or in the presence of a solvent.

Any generally used solvents (organic solvent or aqueous solvent) may be used. Examples of the organic solvent include benzene, toluene, N,N'-dimethylformamide (DMF), dimethyl sulfoxide (DMSO), acetone, chloroform, carbon tetrachloride, tetrahydrofuran (THF), ethyl acetate, chlorobenzene, dichlorobenzene, trifluoro methylbenzene, and anisole. Further, examples of the aqueous solvent include water, and solvents including, as necessary, methanol, ethanol, isopropanol, n-butanol, ethyl cellosolve, butyl cellosolve, and 1-methoxy-2-propanol. Water is preferable.

Any catalyst capable of producing copper(I) ion may be used as the copper catalyst. Examples include copper(I) iodide, copper(I) bromide, and copper sulfate pentahydrate. Copper(I) iodide is preferable.

Generally, sodium ascorbate is used as a reducing agent.

This reaction may be generally performed in a range from room temperature (about 15° C.) to about 80° C., preferably in a range of about 15 to 40° C. The reaction time varies depending on the type of the reaction reagent, the reaction temperature, and the like, and thus cannot be unconditionally stated; however, the reaction is generally completed in about 0.5 to 24 hours.

1-2-4. Azide Group-Containing Glass Substrate

A glass substrate containing an azide group may also be used as the solid-state material. For example, a glass substrate containing an azide group may be produced by first ozone-treating a glass substrate, reacting a silane coupling agent having an amino group with the ozone-treated surface of the glass substrate, thereby introducing the amino group, and causing condensation of the amino group and a azide compound having a carboxyl group.

The ozone treatment is similar to that described in 1-1-4 above.

Examples of the silane coupling agent having an amino group include those described in 1-1-4 above.

Examples of azide compound having a carboxyl group include azidebenzoic acid, 11-azide-3,6,9-trioxaundecanoic acid, 4-azidebenzoic acid, and 4-azidesalicylic acid.

The reaction of reacting a silane coupling agent having an amino group with the ozone-treated surface of the ozone-treated glass substrate, thereby introduce an amino group, and the reaction of causing condensation of the amino group and an azide compound having a carboxyl group are similar to those described in 1-1-4 above.

1-2-5. Joining (Azide-Alkyne Cycloaddition Reaction Between Glass Substrate and Gel)

By performing an azide-alkyne cycloaddition reaction in the contact interfaces of the gel obtained in 1-2-2 and the glass substrate obtained in 1-2-4 above, it is possible to obtain the joined body of the present invention.

The azide-alkyne cycloaddition reaction is performed by bringing the gel obtained in 1-2-2 and the glass substrate obtained in 1-2-4 into contact with each other in the presence of a copper catalyst and a reducing agent. The conditions in this reaction are similar to those in the reaction described in 1-2-3 above.

1-2-6. Carboxy Group- and Host Group-Containing Gel

A gel containing a carboxy group and a host group may be produced, for example, by reacting the compounds represented by Formulas (6) and (7) above, the bi- to tetra-functional crosslinking agent, and the compound represented by Formula (13) below.

[Chem. 13]

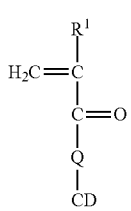
(13)

wherein Q represents O or NH; CD represents α-cyclodextrin, β-cyclodextrin, or γ-cyclodextrin; and $R^1$ represents a hydrogen atom or a methyl group.

The compound represented by Formula (13) above may be produced according to the method disclosed in WO2012/036069.

The method of reacting the compounds represented by Formulas (6), (7), and (13) above and the bi- to tetra-functional crosslinking agent is similar to the method described in 1-1-1 above, i.e., the radical polymerization reaction of the compounds represented by Formulas (2) and (3) and the bi- to tetra-functional crosslinking agent.

1-2-7. Amino Group- and Guest Group-Containing Gel

A gel containing an amino group and a guest group may be produced, for example, by reacting the compound represented by Formula (6) above, the bi- to tetra-functional crosslinking agent, and the compounds represented by Formulas (14) and (15) below.

[Chem. 14]

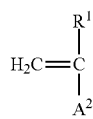

(14)

wherein $A^2$ represents an optionally substituted aryl group, $C(O)OR^b$, or $C(O)NHR^b$; $R^b$ represents an optionally substituted alkyl group, an optionally substituted aryl group, or an optionally substituted arylalkyl group; and $R^1$ represents a hydrogen atom or a methyl group.

[Chem. 15]

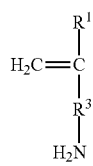

(15)

wherein $R^1$ in Formula (15) above represents a hydrogen atom or a methyl group; and $R^3$ represents an alkylene group or an arylene group.

In Formula (14) above, examples of optionally substituted alkyl group, optionally substituted aryl group, and optionally substituted arylalkyl group represented by $R^b$ include groups similar to those in Formula (3) above.

Further, in Formula (14) above, examples of optionally substituted aryl group represented by $A^2$ include groups similar to those as in Formula (3) above.

Preferable examples of the compound represented by Formula (14) above include acrylamide, n-butyl acrylate, t-butyl acrylate, N-(1-adamantyl)acrylamide, N-benzylacrylamide, N-1-naphthylmethylacrylamide, styrene, ethyl acrylate, butyl acrylate, hexyl acrylate, lauryl acrylate, octadecyl acrylate, t-butyl acrylate, isobutyl acrylate, 2-hydroxyethyl acrylate, hydroxypropyl acrylate, 4-hydroxybutyl acrylate, 2-carboxyethyl acrylate, di(ethyleneglycol) ethylether acrylate, di(ethyleneglycol)2-ethylhexylether acrylate, poly(propyleneglycol)acrylate, poly(ethyleneglycol)methylethyl acrylate, N,N-dimethyl acrylamide, N-isopropylacrylamide, N-tert-butyl acrylamide, N-hydroxymethyl acrylamide, N-hydroxyethyl acrylamide, N-[tris(hydroxymethyl)methyl]acrylamide, N-(3-methoxypropyl) acrylamide, glycidyl methacrylate, methacrylic acid N-hydroxysuccinimide ester, triethyleneglycol methylester methacrylate, methyl methacrylate, ethyl methacrylate, 2,2,2-trifluoroethyl methacrylate, butyl methacrylate, 2-hydroxyethyl methacrylate, 2-hydroxyethyl methacrylate, hydroxypropyl methacrylate, 2-aminoethyl methacrylate hydrochloride, and 2-(dimethylamino)ethyl methacrylate.

Further, only one kind of the compound represented by Formula (14) above, or two or more kinds of the compound represented by Formula (14) above may be used.

The compound represented by Formula (14) above may be produced according to the method disclosed in WO2012/036069.

In Formula (15) above, examples of alkylene group and arylene group represented by $R^3$ include groups similar to those in Formula (12) above.

Preferable examples of the compound represented by Formula (15) above include allylamine, styreneamine, 3-vinylaniline, and 2-aminoethyl methacrylate hydrochloride. Known compounds may be used as the compounds represented by Formula (15) above. Further, only one kind of the compound represented by Formula (15) above, or two or more kinds of the compound represented by Formula (15) above may be used.

The method of reacting the compounds represented by Formulas (6), (14), and (15) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

1-2-8. Joining (Amidation Reaction and Host-Guest Interaction)

By bringing the gels obtained in 1-2-6 and 1-2-7 above into contact with each other, a host-guest interaction occurs between the gels. Thereafter, by performing an amidation reaction in the contact interfaces of the gels, the joined body of the present invention may be produced.

Specific examples of the method of bringing the gels into contact with each other include a method of bringing the gels into contact with each other in an aqueous solvent, and then leaving the gels unattended; and a method of placing the gels in an aqueous solvent, and bringing the gels into contact with each other by shaking or stirring.

Examples of the aqueous solvent include water; an aqueous solution containing, as necessary, sodium phosphate, sodium carbonate, or like salts; and a mixed solvent of water and alcohol etc. Water is preferable.

Any method may be used as the method of shaking or stirring the gels, insofar as the gels come closer within a certain distance. For example, a method of using a stirrer or a shaking apparatus, such as a vortex mixer or a shaker, or a method of irradiating the gels with an ultrasonic wave may be used.

The amidation reaction is performed using a condensing agent in the interfaces of the gels on which the above host-guest interaction occurs. This reaction may be performed without a solvent, or in the presence of a solvent.

Any generally used solvents (organic solvent or aqueous solvent) may be used. Examples of the organic solvent include benzene, toluene, N,N-dimethylformamide (DMF), dimethyl sulfoxide (DMSO), acetone, chloroform, carbon tetrachloride, tetrahydrofuran (THF), ethyl acetate, chlorobenzene, dichlorobenzene, trifluoro methylbenzene, and anisole. Further, examples of the aqueous solvent include water; and solvents including, as necessary, methanol, ethanol, isopropanol, n-butanol, ethyl cellosolve, butyl cellosolve, and 1-methoxy-2-propanol.

The amount of the solvent may be suitably adjusted; however, the amount of the solvent is, for example, generally 0.1 to 1 liter, preferably 0.2 to 0.5 liter, per mol of the total monomer used for the polymerization.

This reaction may be performed generally in a range from room temperature (about 15° C.) to 90° C., preferably in a range of about 20 to 40° C. The reaction time varies depending on the type of the reaction reagent, the reaction temperature, and the like, and thus cannot be unconditionally stated; however, the reaction is completed generally in about 4 to 24 hours.

2. Coordinate Bond

When the chemical bond in the joined body of the present invention is a coordinate bond, the joining and the dissociation are reversible; that is, the joining and the dissociation can be controlled.

Examples of coordinate bond include metal-ligand interaction, and apoenzyme-cofactor interaction. The joined body may have only one of these bonds, or two or more kinds of these bonds. When, in particular, the coordinate bond is apoenzyme-cofactor interaction, a catalytic activity may be added to the joined body. The catalytic activity may be artificially controlled.

Examples of metals for metal-ligand interaction include iron, zinc, manganese, magnesium, copper, cobalt, platinum, and titanium.

Examples of ligands for metal-ligand interaction include imidazole, pyridine, amino group, and chloro group.

Examples of apoenzymes for apoenzyme-cofactor interaction include hemoglobin, cytochrome, nitric oxide synthetase, phosphatase, catalase, hydrogenase, peroxidase, DNA polymerase, alcohol dehydrogenase, and carbonic anhydrase.

Examples of cofactors for apoenzyme-cofactor interaction include iron, manganese, copper, cobalt, zinc, selenium, molybdenum, calcium, metal porphyrin, vitamin $B_1$, vitamin $B_2$, vitamin $B_6$, vitamin $B_{12}$, vitamin C, and adenosine triphosphate.

When the chemical bond is a coordinate bond, examples of usable solid-state materials include any of the above-listed materials, i.e., gels (hydrogel, organogel), glass, wooden plates, plastic, metal plates (gold, iron, palladium, platinum, silver, aluminum, or the like), and paper. However, gels are particularly preferable.

Examples of the gels include a gel having the repeating units represented by Formula (1) above, and a crosslinking agent.

When a gel having the repeating units represented by Formula (1) above and a crosslinking agent is used as the solid-state material, a joined body may be produced by introducing a group capable of forming a coordinate bond into individual gels, and then reacting the groups.

For example, by introducing an apoenzyme into one of the gels to be joined while introducing a cofactor into the other gel, and bringing the gels into contact with each other, it is possible to produce a joined body.

2-1. Apoenzyme Group-Containing Gel

Figure 12:
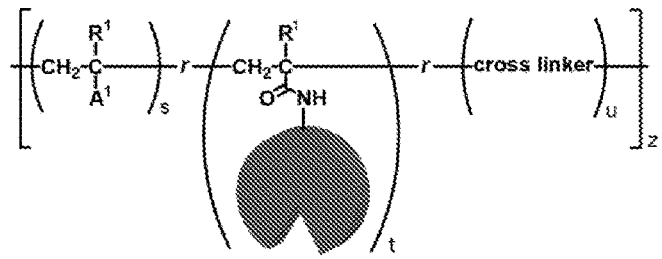
FIG. 12 is a structural depiction of a gel in which an apoenzyme is introduced and is, for example, represented by Formula (16), in which apohorseradish peroxidase is used as the apoenzyme.

The gel in which an apoenzyme is introduced is, for example, represented by Formula (16), as shown in FIG. 12, in which apohorseradish peroxidase is used as the apoenzyme.

In Formula (16), $R^1$ is the same or different, and each represents a hydrogen atom or a methyl group; $A^1$ represents an optionally substituted aryl group, $C(O)NHR^a$, or $C(O)OR^b$; $R^a$ represents a hydrogen atom, an optionally substituted alkyl group, an optionally substituted aryl group, or an optionally substituted arylalkyl group; $R^b$ represents an optionally substituted alkyl group, an optionally substituted aryl group, or an optionally substituted arylalkyl group; "cross-linker" represents a bi- to tetra-functional crosslinking agent; $s+t+u=100$ mol % wherein s is 1 to 98.9, t is 0.1 to 98, and u is 1 to 98.9; z is 2 to 10,000,000; and -r- represents a random bond.

In the gel represented by Formula (16) above, the ratio s:t:u is preferably 98.9:0.1:1 to 85:10:5 (mol % ratio). Particularly preferably, the ratio s:t:u is 97.5:0.5:2 to 96.5:1.5:2 (mol % ratio).

The gel having the apohorseradish peroxidase represented by Formula (16) above may be produced, for example, by reacting the compounds represented by Formulas (6) and (7) above, and the bi- to tetra-functional crosslinking agent, and then leading the apohorseradish peroxidase to the carboxy group derived from the compound represented by Formula (7). For example, by reacting the carboxy group derived from the compound represented by Formula (7) and the amino group present in the apohorseradish peroxidase, it is possible to produce a gel containing the apohorseradish peroxidase represented by Formula (16) above.

The method of reacting the compounds represented by Formulas (6) and (7) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

Subsequently, the carboxy group derived from the compound represented by Formula (7) above is reacted with the apohorseradish peroxidase, thereby obtaining a gel containing the apohorseradish peroxidase represented by Formula (16) above. In general, a polymer obtained by reacting the compounds represented by Formulas (6) and (7) above and the bi- to tetra-functional crosslinking agent; a dehydration condensation agent; and a carboxylic acid activator are mixed and stirred in a buffer solution, and the resulting gel is mixed and stirred with apohorseradish peroxidase.

Examples of buffer solution include 2-morpholinoethane sulfonic acid buffer solution (MES buffer), phosphate buffer solution, and citric acid buffer solution. MES buffer is preferable.

Generally, 1-ethyl-3-(3-dimethylaminopropyl)carbodiimide hydrochloride (EDC) is used as the dehydration condensation agent.

Examples of carboxylic acid activator include 1-hydroxy-2,5-dioxopyrrolidine-3-sulfonic acid sodium salt, 1-hydroxybenzotriazole, 1-hydroxy-7-azabenzotriazole, pentafluorophenol, N-hydroxysuccinimide, N-bromosuccinimide, N-chlorosuccinimide, and N-iodosuccinimide. 1-Hydroxy-2,5-dioxopyrrolidine-3-sulfonic acid sodium salt (sulfo-NHS) is preferable.

The amount of the buffer solution may be suitably adjusted; however, the amount of the buffer solution is, for example, generally 1 to 100 liters, preferably 10 to 50 liters, per mol of the monomer used for the dehydration condensation.

The reaction of the polymer obtained by reacting the compounds represented by Formulas (6) and (7) above and the bi- to tetra-functional crosslinking agent; a dehydration condensation agent; and a carboxylic acid activator may be generally performed in a range from room temperature (about 15° C.) to 40° C., preferably in a range of about 35 to 37° C. The reaction time varies depending on the type of the reaction reagent, the reaction temperature, and the like, and thus cannot be unconditionally stated; however, the reaction is generally completed in about 8 to 24 hours.

Further, the reaction of the gel obtained above and apohorseradish peroxidase may be generally performed in a range from room temperature (about 15° C.) to 40° C., preferably in a range of about 35 to 37° C. The reaction time varies depending on the reaction temperature, and the like, and thus cannot be unconditionally stated; however, the reaction is generally completed in about 8 to 24 hours.

2-2. Cofactor-Containing Gel

Figure 13:
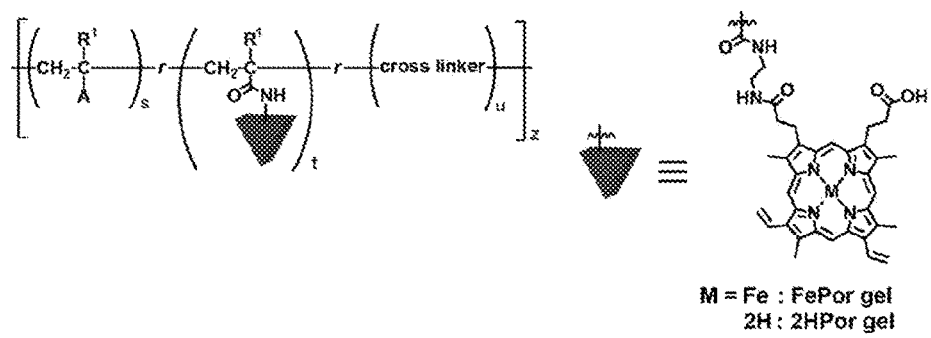
FIG. 13 is a structural depiction of a gel in which a cofactor is introduced and is represented, for example, by Formula (17), in which iron porphyrin is used as the cofactor.

The gel in which a cofactor is introduced is represented, for example, by Formula (17), as shown in FIG. 13, in which iron porphyrin is used as the cofactor.

In Formula (17), $R^1$ is the same or different, and each represents a hydrogen atom or a methyl group; A represents an optionally substituted aryl group, $C(O)OR^a$, or $C(O)NHR^a$; $R^a$ represents a hydrogen atom, an optionally substituted alkyl group, an optionally substituted aryl group, or an optionally substituted arylalkyl group; "cross-linker" represents a bi- to tetra-functional crosslinking agent; s+t+u=100 mol % wherein s is 1 to 98.9, t is 0.1 to 98, and u is 1 to 98.9; z is 2 to 10,000,000; and -r- represents a random bond.

In the gel represented by Formula (17) above, the ratio s:t:u is preferably 98.9:0.1:1 to 85:10:5 (mol % ratio). Particularly preferably, the ratio s:t:u is 97.5:0.5:2 to 96.5:1.5:2 (mol % ratio).

The gel having the iron porphyrin represented by Formula (17) above may be produced, for example, by reacting the compound represented by Formula (3) above, the bi- to tetra-functional crosslinking agent, and the compound represented by Formula (18) above, and then leading the iron porphyrin to the succinimide group derived from the compound represented by Formula (18) below.

[Chem. 18]

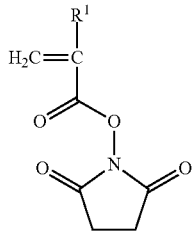

(18)

wherein $R^1$ in Formula (18) above represents a hydrogen atom or methyl group.

Known compounds may be used as the compound represented by Formula (18) above. Only one kind or two or more kinds may be used. In particular, N-succinimidyl acrylate (NHS-AAm) is preferable.

The method of reacting the compounds represented by Formulas (3) and (18) above and the bi- to tetra-functional crosslinking agent is similar to the method in 1-1-1 above, i.e., the radical polymerization reaction of the compounds represented by Formulas (3) and (4) and the bi- to tetra-functional crosslinking agent. A photopolymerization initiator is used as a radical polymerization initiator.

Examples of photopolymerization initiators include 2-ketoglutaric acid, dibenzoyl, acetophenone, 2,2-dimethoxy-1,2-diphenylethan-1-one, 1-hydroxy-cyclohexyl-phenyl-ketone, bis(4-tert-butylphenyl)iodonium hexafluorophosphate, diphenyliodonium hexafluorophosphate, and nifedipine. 2-ketoglutaric acid is preferable.

Subsequently, the succinimide group derived from the compound represented by Formula (18) above is reacted with an iron porphyrin compound having an amino group, thereby obtaining a gel containing iron porphyrin. Generally, a polymer obtained by reacting the compounds represented by Formulas (3) and (18) above and the bi- to tetra-functional crosslinking agent is mixed and stirred with an iron porphyrin compound having an amino group in an organic solvent.

Examples of organic solvent include benzene, toluene, N,N-dimethylformamide (DMF), dimethyl sulfoxide (DMSO), acetone, chloroform, carbon tetrachloride, tetrahydrofuran (THF), ethyl acetate, chlorobenzene, dichlorobenzene, trifluoro methylbenzene, and anisole.

Examples of porphyrin compound having an amino group include 5,10,15,20-tetrakis(4-aminophenyl)-21H,23H-porphine (FePor) and the like. FePor is preferable.

This reaction may be performed generally in a range from room temperature (about 15° C.) to 60° C., preferably in a range of about 15 to 30° C. The reaction time varies depending on the type of the reaction reagent, the reaction temperature, and the like, and thus cannot be unconditionally stated; however, the reaction is generally completed in about 12 to 24 hours.

2-3. Joining

By bringing the gels obtained in 2-1 and 2-2 above into contact with each other, it is possible to obtain the joined body of the present invention.

Specific example of the method for bringing the gels into contact with each other include a method of bringing the gels into contact with each other in air or in an aqueous solvent at an enzyme-activating temperature, and then leaving the gels unattended.

The enzyme-activating temperature depends on the type of enzyme; however, the enzyme-activating temperature is generally about 10° C. to 40° C., in particular, about 30 to 37° C. for apohorseradish peroxidase.

Examples of the aqueous solvent include water; an aqueous solution containing, as necessary, phosphate or a salt such as sodium carbonate; and a mixed solvent of water and alcohol etc. A phosphoric acid aqueous solution is preferable.

3. Noncovalent Bond

In the joined body of the present invention, when the chemical bond is a noncovalent bond, the joining and the dissociation are reversible; that is, the joining and the dissociation can be controlled.

Examples of the noncovalent bond include hydrogen bond, ion-ion interaction, ion-dipole interaction, cation-π interaction, π-π interaction, Van der Waals' force, hydrophobic interaction, and host-guest interaction. Hydrogen bond and host-guest interaction are preferable. A case of hydrogen bond is described below as an example.

Specific examples of hydrogen bond include complementary interaction between nucleic acid bases. When the complementary interaction between nucleic acid bases is used as a hydrogen bond, the joining can be accomplished selectively and significantly precisely.

When the chemical bond is a hydrogen bond, examples of solid-state materials include any of above-listed materials, i.e., gels (hydrogel, organogel), glass, wooden plates, plastic, metal plates (gold, iron, palladium, platinum, silver, aluminum, or the like), and paper. Of these, gels are particularly preferable.

Examples of the gels include a gel having the repeating units represented by Formula (1) below and a crosslinking agent.

When a gel having the repeating units represented by Formula (1) above and a crosslinking agent is used as the solid-state material, a joined body may be produced by introducing a group capable of forming a hydrogen bond into individual gels, and then reacting the groups.

For example, by introducing a nucleic acid base into one of the gels to be joined while introducing another nucleic acid base complementary to the above nucleic acid base into the other gel, and bringing these gels into contact with each other, it is possible to produce a joined body.

A joined body may also be produced by introducing an oligonucleotide into one of the gels to be joined and introducing another oligonucleotide complementary to the above oligonucleotide into the other gel, and bringing these gels into contact with each other.

3-1. Nucleic Acid Base

When a gel having the repeating units represented by Formula (1) above and the crosslinking agent is used as a solid-state material, the gel containing a nucleic acid base is represented, for example, by Formula (19) below.

[Chem. 19]

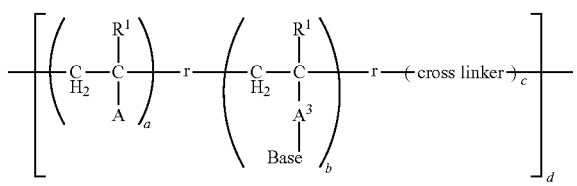

(19)

wherein $R^1$ is the same or different, and each represents a hydrogen atom or a methyl group; A represents an optionally substituted aryl group, $C(O)OR^a$, or $C(O)NHR^a$; $R^a$ represents a hydrogen atom, an optionally substituted alkyl group, an optionally substituted aryl group, or an optionally substituted arylalkyl group; $A^3$ represents an alkylene group, an arylene group, $C(O)O$, or $C(O)NH$; "Base" represents adenine, thymine, uracil, guanine, or cytosine; "crosslinker" represents a bi- to tetra-functional crosslinking agent; a+b+c=100 mol % wherein a is 60 to 98, b is 1 to 20, and c is 1 to 20; d is 2 to 10,000,000; and -r- represents a random bond.

In the gel represented by Formula (19) above, the ratio a:b:c is preferably 98:1:1 to 60:20:20 (mol % ratio). Particularly preferably, the ratio a:b:c is 85:5:10 to 75:10:15 (mol % ratio).

The gel containing a nucleic acid base represented by Formula (19) above may be produced, for example, by reacting the compound represented by Formula (1) above, the bi- to tetra-functional crosslinking agent, and the compound represented by Formula (20) below.

[Chem. 20]

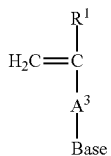

(20)

wherein $R^1$ represents a hydrogen atom or a methyl group; $A^3$ represents an alkylene group, an arylene group, $C(O)O$, or $C(O)NH$; and "Base" represents adenine, thymine, uracil, guanine, or cytosine.

In Formula (20) above, examples of the alkylene group and arylene group represented by $R^3$ include groups similar to those in Formula (12) above.

The gel containing a nucleic acid base represented by Formula (19) above is produced by subjecting the compounds represented by Formulas (3) and (20) above and the bi- to tetra-functional crosslinking agent to radical polymerization. Generally, the compounds represented by Formulas (3) and (20), the above bi- to tetra-functional crosslinking agent, and, if necessary, a radical polymerization initiator are mixed and stirred in a container substituted with inert gas, or a vacuum-deaerated container.

The method of reacting the compounds represented by Formulas (3) and (20) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

The combination of the bases in Formula (20) is any pair of complementary nucleic acid bases. A combination of adenine-thymine is described below.

3-1-1. Adenine-Containing Gel

In the compound represented by Formula (20) above, a compound containing adenine as the "Base" is produced, for example, by reacting adenine with a halogenated alkylstyrene derivative. Generally, a reaction accelerator, a polymerization-inhibitor, a halogenated alkylstyrene derivative, and adenine are mixed and stirred in a solvent.

The reaction may be performed without a solvent, or with a solvent (organic solvent or aqueous solvent) generally used for organic synthesis reactions. Examples of the organic solvent include dimethyl sulfoxide (DMSO) and dimethylformamide (DMF). Examples of the aqueous solvent include water; and buffers containing, as necessary, a salt such as sodium phosphate or sodium carbonate. When a solvent is used, the amount of the solvent is suitably adjusted.

Subsequently, the compound represented by Formula (20) above having adenine as the "Base," the compound represented by Formula (3) above, and the bi- to tetra-functional crosslinking agent were subjected to radical polymerization as explained above, thereby producing a gel represented by Formula (19) having adenine as the "Base."

3-1-2. Thymine-Containing Gel

In the compound represented by Formula (20) above, a compound containing thymine as the "Base" is produced, for example, in the same manner as in 3-1-2 above, except that thymine is used instead of adenine.

The resulting compound represented by Formula (20) above containing thymine as the "Base," the compound represented by Formula (3) above, and the bi- to tetra-functional crosslinking agent are subjected to radical polymerization as described above, thereby producing a gel represented by Formula (19) above containing thymine as the "Base."

3-1-3. Joining

By bringing the gels obtained in 3-1-1 and 3-1-2 above into contact with each other, it is possible to obtain the joined body of the present invention.

Specific examples of the method for bringing the gels into contact with each other include a method of placing the gels in an organic solvent, and bringing the gels into contact with each other by shaking or stirring.

Examples of the organic solvent include chloroform, dichloromethane, ethyl acetate, diethylether, toluene, and hexane. Chloroform and toluene are preferable.

Any method may be used to shake or stir the gels, insofar as the gels come closer within a certain distance. For example, a method of using a stirrer or a shaking apparatus, such as a vortex mixer or shaker, or a method of irradiating the gels with an ultrasonic wave may be used.

3-2. Oligonucleotide 3-2-1. Oligonucleotide-Containing Gel

Figure 14:
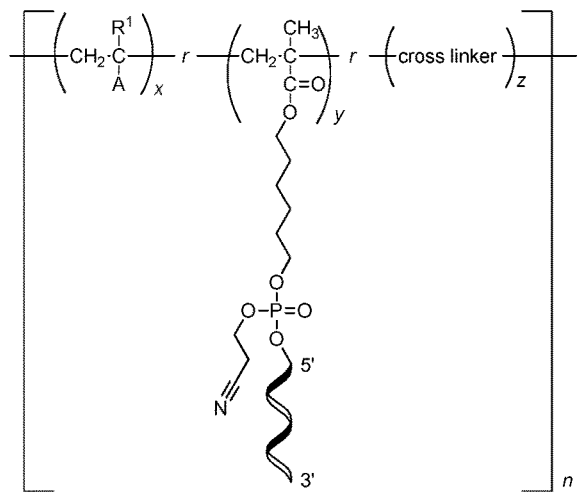
FIG. 14 is a structural deptiction of a gel containing an oligonucleotide of Formula (21)

When a gel containing the repeating units represented by Formula (1) above and a crosslinking agent is used as a solid-state material, the gel containing oligonucleotide is represented, for example, by Formula (21, as shown in FIG. 14.

In Formula (21), $R^1$ is the same or different, and each represents a hydrogen atom or a methyl group; A represents an optionally substituted aryl group, $C(O)OR^a$, or $C(O)NHR^a$; $R^a$ represents a hydrogen atom, an optionally substituted alkyl group, an optionally substituted aryl group, or an optionally substituted arylalkyl group; the site represented by 5'-3' represents an oligonucleotide having an arbitrary sequence consisting of five bases: adenine, thymine, uracil, guanine, and cytosine; "cross-linker" represents a bi- to tetra-functional crosslinking agent; x+y+z=100 mol % wherein x is 60 to 99.899, y is 0.001 to 20, and z is 0.1 to 20; n is 2 to 10,000,000; and -r- represents a random bond.

In the gel represented by Formula (21) above, the ratio x:y:z is preferably 99.899:0.001:0.1 to 60:20:20 (mol % ratio). Particularly preferably, the ratio x:y:z is 99.698:0.002:0.3 to 98.995:0.005:1 (mol % ratio).

Figure 15:
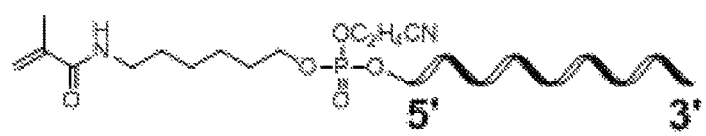
FIG. 15 is a structural depiction of a compound of Formula (22).

The gel containing the oligonucleotide represented by Formula (21) above may be produced, for example, by reacting the compound represented by Formula (3) above, the bi- to tetra-functional crosslinking agent, and the compound represented by Formula (22), as shown in FIG. 15.

In Formula (22), the site represented by 5'-3' represents an oligonucleotide having an arbitrary sequence consisting of five bases: adenine, thymine, uracil, guanine, and cytosine.

"Oligonucleotide" is a nucleotide (DNA or RNA) sequence of about 4 to 20 nt.

The compound represented by Formula (22) above is produced, for example, by reacting deoxyribonucleotide with phosphate amidite. Generally, a carrier is bonded via the hydroxy group at the 3'-end of nucleotide, the protecting group of a hydroxy group at the 5'-end is removed, and a base in which the hydroxy group at the 5'-end is protected and the hydroxy group at the 3'-end is converted to a trivalent phosphate amidite derivative is reacted to cause phosphodiester bond, thus sequentially synthesizing oligonucleotides. Finally, a phosphate amidite compound having a polymerization group at the end is reacted, thereby synthesizing an oligonucleotide having a polymerization group at the end.

The reaction may be performed with a solvent (organic solvent or aqueous solvent) generally used for organic synthesis reactions. Examples of the organic solvent include dimethyl sulfoxide (DMSO), dimethylformamide (DMF), and acetonitrile. Examples of the aqueous solvent include water, and buffers containing, as necessary, a salt such as sodium phosphate or sodium carbonate. When a solvent is used, the amount of the solvent is suitably adjusted.

The method of reacting the compounds represented by Formulas (3) and (22) above and the bi- to tetra-functional crosslinking agent is similar to the method in 1-1-1 above, i.e., the radical polymerization reaction of the compounds represented by Formulas (3) and (4) and the bi- to tetra-functional crosslinking agent.

3-2-2. Joining

By bringing the gels obtained in 3-2-1 above into contact with each other, it is possible to obtain the joined body of the present invention.

Specific examples of the method of bringing the gels into contact with each other include a method of directly bringing the gels together in air, and a method of placing the gels in water and bringing the gels into contact with each other by shaking or stirring.

Any method may be used to shake or stir the gels, insofar as the gels come closer within a certain distance. For example, a method of using a stirrer or a shaking apparatus, such as a vortex mixer or shaker, or a method of irradiating the gels with an ultrasonic wave may be used.

EXAMPLES

Hereunder, the present invention is more specifically explained with reference to specific examples. The present invention is not limited to the examples below, and may be carried out with appropriate modifications within a scope in which the gist of the present invention is maintained.

Measurement Apparatus

In the Examples and Comparative Examples, physical properties were measured in the following manner Measurement of Rupture Stress Measurement Instrument: RE-33005B creep meter, produced by Yamaden Co., Ltd.

Measurement Conditions: Sweep rate: 0.05-0.1 mm/sec

Tensile Strength Measurement

Measurement Instrument: Creep meter (Rheoner RE-33005B), produced by Yamaden Co., Ltd.

Measurement Conditions: Sweep rate: 0.05-0.1 mm/sec

Measurement of $^1$H-NMR

Measurement Instrument: ECA500 (solution NMR), produced by JEOL Ltd., JEOL JNM-ECA 400 NMR spectrometer (Solid $^1$H Field Gradient Magic Angle Spinning (FG-MAS) NMR)

Measurement Temperature: 30° C.

Solvent: $CDCl_3$, DMSO-$d_6$, $D_2O$

Joined Body Joined by Covalent Bond

Example 1 (Solid-State Material: Gel, Covalent Bond: Carbon-Carbon Bond)

(1) Synthesis of Gel (1-1) Synthesis of Boronic Acid-Containing Hydrogel

[Chem. 23]

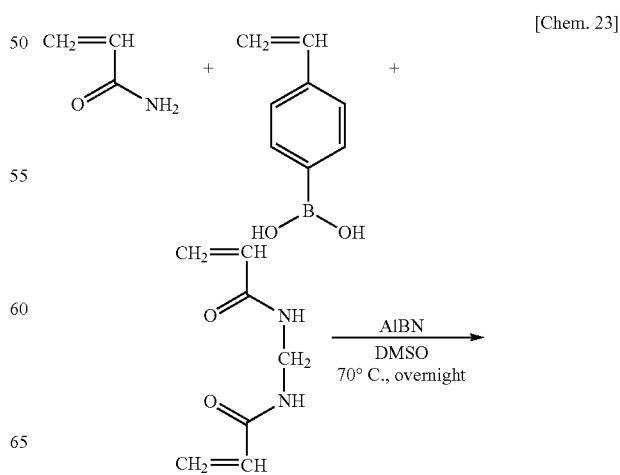

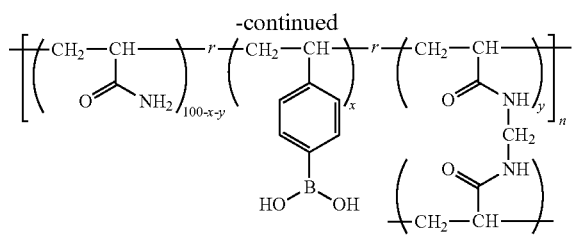

-continued

Acrylamide (AAm) (183 mg, 2.6 mmol), 4-phenylboronic acid (44 mg, 0.3 mmol), N,N'-methylene-bis-acrylamide (MBAAm) (19 mg, 0.12 mmol), and 2,2'-azobis (isobutyronitrile) (AIBN) (2.5 mg, 0.015 mmol) were dissolved in DMSO (1.5 mL), and subjected to argon bubbling for an hour, followed by reaction overnight at 70° C. to produce a gel. The resulting gel was washed with DMSO, and immersed in water. In the resulting gel, the ratio between 4-phenylboronic acid-derived unit: MBAAm derived unit was 10:4 (mol composition ratio). FIG. 1 shows $^1$H-FGMAS NMR (JEOL JNM-ECA 400 NMR spectrometer, $D_2O$, 30° C.) data of the obtained gel.

(1-2) Synthesis of Aryl Halide Group-Containing Hydrogel between aryl halide group-modified acrylic acid-derived unit:MBAAm-derived unit was 10:2 (mol composition ratio). FIG. 1 shows $^1$H-FGMAS NMR data (JEOL JNM-ECA 400 NMR spectrometer, $D_2O$, 30° C.) of the obtained gel.

(2) Joining (Suzuki-Miyaura Coupling)

Each gel obtained in (1-1) and (1-2) above was cut to a size of 4 mm×3 mm×2 mm, and the 4 mm×3 mm plane was used as the contact surface. The two gels were brought together at their contact surfaces, and immersed in a potassium carbonate aqueous solution (0.1 g/mL). Palladium acetate dissolved in acetone was added thereto, and the gels were left unattended for an hour. As a result, the gels were joined at their contact surfaces.

Comparative Example 1

In Example 1 (2), the gels were left unattended for an hour without adding palladium acetate dissolved in acetone. As a result, the gels were not joined.

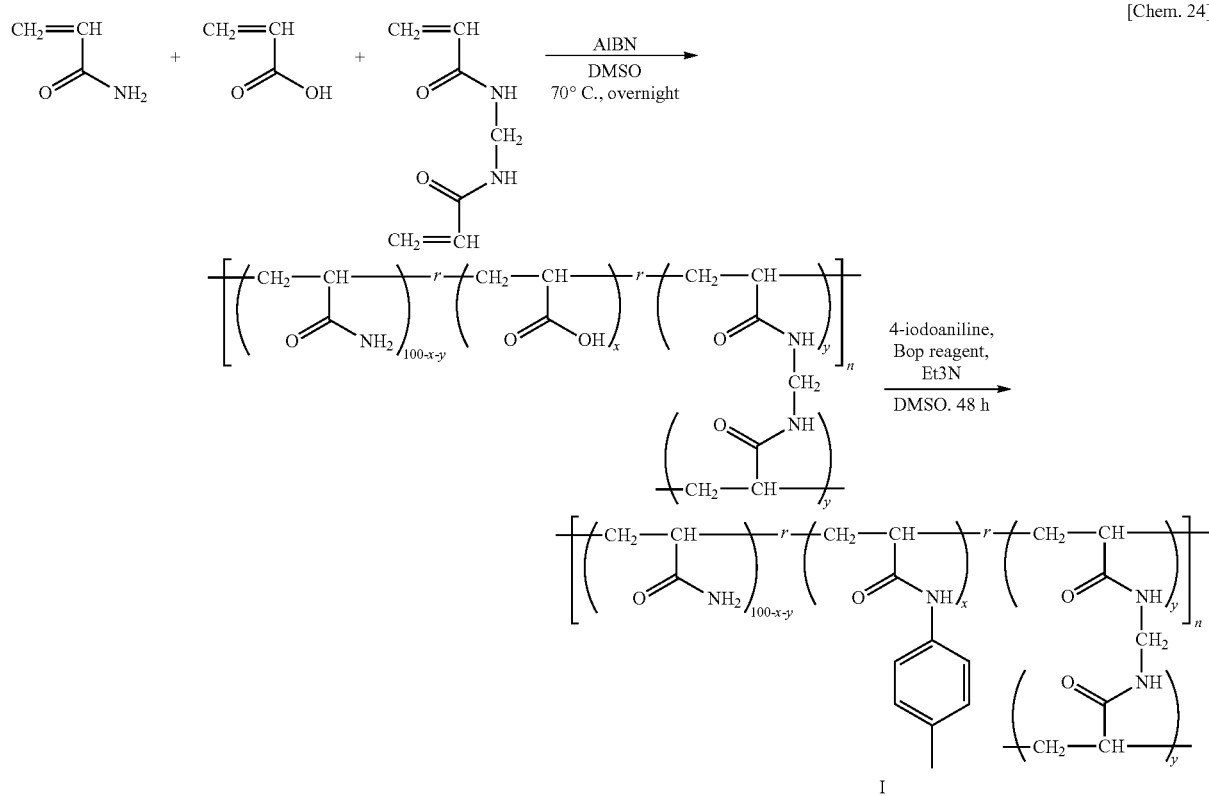

[Chem. 24]

AAm (183 mg, 2.6 mmol), acrylic acid (AA) (20.6 µL, 0.3 mmol), MBAAm (19 mg, 0.12 mmol), and AIBN (2.5 mmol, 0.015 mmol) were dissolved in DMSO (1.5 mL), and subjected to argon bubbling for an hour, followed by reaction overnight at 70° C. to produce a gel. The resulting gel was immersed in a DMSO solution in which 4-iodoaniline (197 mg, 0.9 mmol), benzotriazole-1-yloxy-tris dimethylamino phosphonium salt (Bop reagent) (39 mg, 0.9 mmol), and triethylamine (124 µL, 0.9 mmol) were dissolved, and reacted for 48 hours. The resulting gel was washed with DMSO, and immersed in water. In the resulting gel, the ratio Comparative Example 2

The same procedures as in Example 1 were performed, except that the gels were produced without using acrylic acid in (1-2). As a result, the gels were not joined.

Comparative Example 3

The same procedures as in Example 1 were performed, except that the gels were joined without the condensation of 4-iodoaniline in (1-2). As a result, the gels were not joined.

Test Example 1 (Evaluation of Joining Strength)

Figure 2:
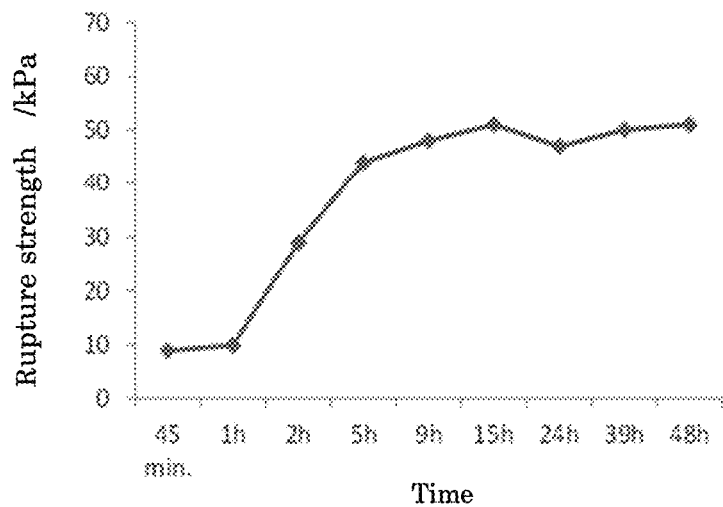
FIG. 2 is a graph showing a time-dependent change in the value of stress, according to Test Example 1.

Each gel obtained in (1-1) and (1-2) in Example 1 was cut to a size of 4 mm×3 mm×2 mm, and the 4 mm×3 mm plane was used as the contact surface. Several joined gels were prepared by bringing two gels together at their contact surfaces, immersing the gels in a potassium carbonate aqueous solution (0.1 g/mL), adding palladium acetate dissolved in acetone to the solution, and leaving these joined gels unattended for 45 minutes, 1 hour, 2 hours, 5 hours, 9 hours, 15 hours, 24 hours, 39 hours, and 48 hours, respectively. The stresses at breakage of the respective joined gels were measured to find a change in stress with time. FIG. 2 shows the results.

Test Example 2 (Evaluation of Joining Strength Depending on Substituent Introduction Amount)

(1) In Example 1 (1-1), the ratio of the amount of 4-phenylboronic acid to the amount of MBAAm (hereinafter referred to as "amount of 4-phenylboronic acid:amount of MBAAm") are changed to "9 mg (0.06 mmol):19 mg (0.12 mmol)," "22 mg (0.15 mmol):19 mg (0.12 mmol)," "66 mg (0.45 mmol):19 mg (0.12 mmol)," and "88 mg (0.6 mmol): 19 mg (0.12 mmol)," thereby obtaining gels in which 4-phenylboronic acid-derived unit:MBAAm-derived unit were (2:4), (5:4), (15:4), and (20:4), respectively (mol composition ratio).

(2) Similarly, in Example 1 (1-2), the ratio of the amount of acrylic acid to the amount of MBAAm (hereinafter referred to as "amount of acrylic acid:amount of MBAAm") was changed to "4.1 μm (0.06 mmol):19 mg (0.12 mmol)," "10.3 μm (0.15 mmol):19 mg (0.12 mmol)," "30.9 μm (0.45 mmol):19 mg (0.12 mmol)," and "41.2 μm (0.6 mmol):19 mg (0.12 mmol)," respectively, thereby obtaining gels in which aryl halide group-modified acrylic acid-derived unit: MBAAm-derived unit were (2:2), (5:2), (15:2), and (20:2), respectively (mol composition ratio).

Figure 3:
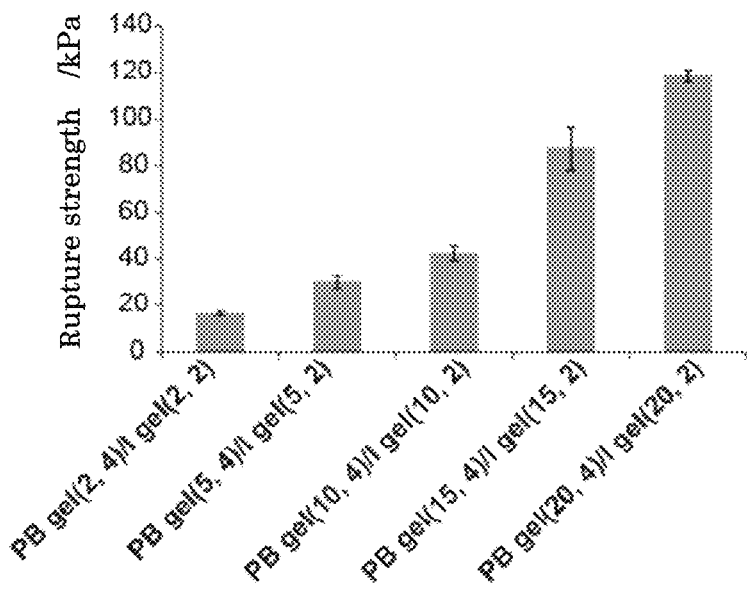
FIG. 3 is a graph showing a change in rupture stress depending on a substituent introduction amount, according to Test Example 2.

(3) Among the gels obtained in (1) and (2), the gels with an identical introduction ratio of the boronic acid and the aryl halide group were left unattended for 24 hours in the same manner as in Example 1 (2), thereby joining the gels. The rupture stresses of the resulting four kinds of gels and the gels obtained in Example 1 (2) were measured. FIG. 3 shows the results.

Example 2 (Solid-State Material: Gel, Covalent Bond: Carbon-Nitrogen Bond)

(1) Synthesis of Gel
(1-1) Synthesis of Substituent (N-(2-aminoethyl)-4-azidebenzamide) to be Introduced N-hydroxysuccinimide (348 mg, 3 mmol) and 4-azidebenzoic acid (500 mg, 3 mmol) were dissolved in a mixed solvent of dichloromethane/N,N-dimethylformamide:1/1 (v/v), and 1-ethyl-3-(3-dimethylaminopropyl) carbodiimide hydrochloride (EDC) (385 mg, 4 mmol) was added thereto under ice-cooling. The mixture was heated to room temperature, and stirred overnight. Subsequently, dichloromethane was distilled off, ice water was added, and precipitated solid was collected by filtration. Recrystallization was performed using ethyl acetate, and the resulting crystal was dissolved in 50 mL of dichloromethane, added dropwise to an ethylenediamine (12.5 mmol)-dichloromethane solution (200 mL), and stirred for 24 hours. Using dichloromethane: ethanol (2:1 v/v) and a small amount of ammonia water, the target substance was purified by silica gel column chromatography.

(1-2) Synthesis of Azide Group-Containing Hydrogel

[Chem. 25]

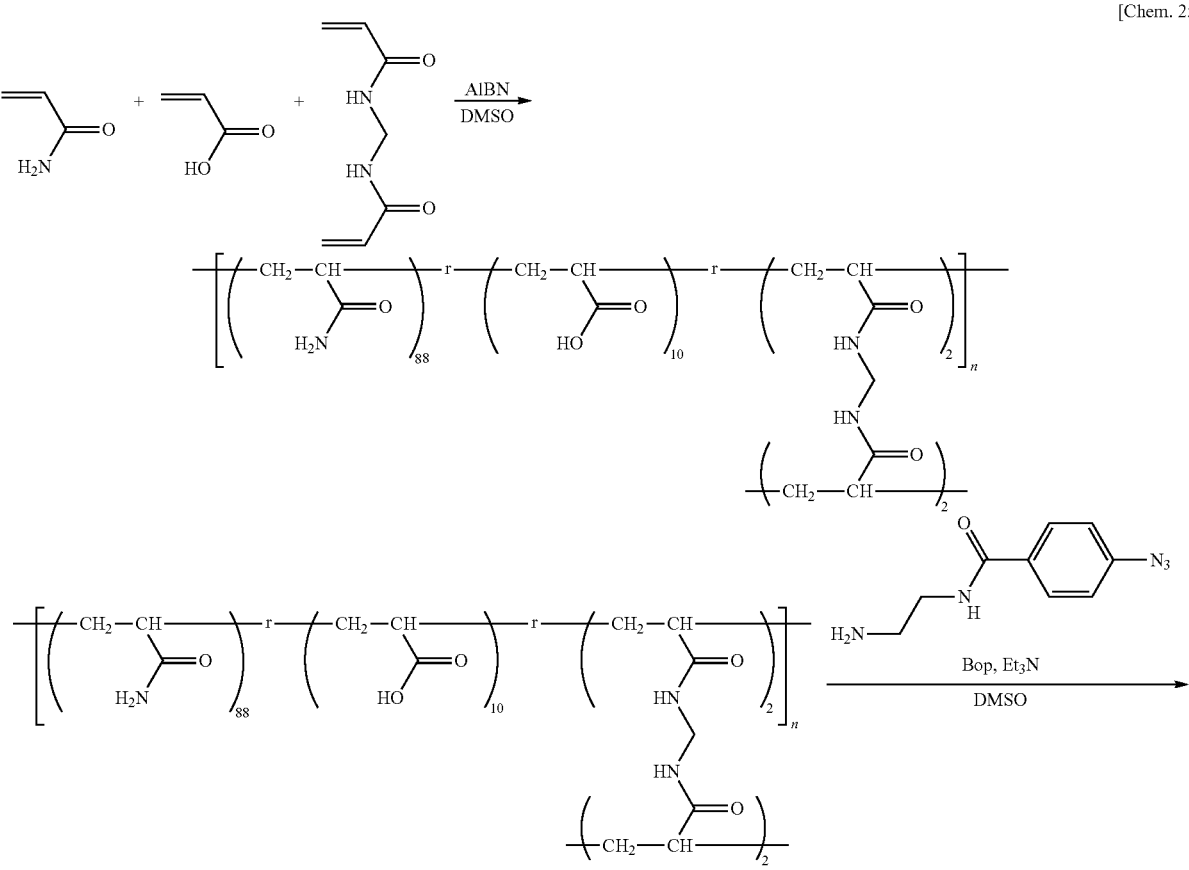

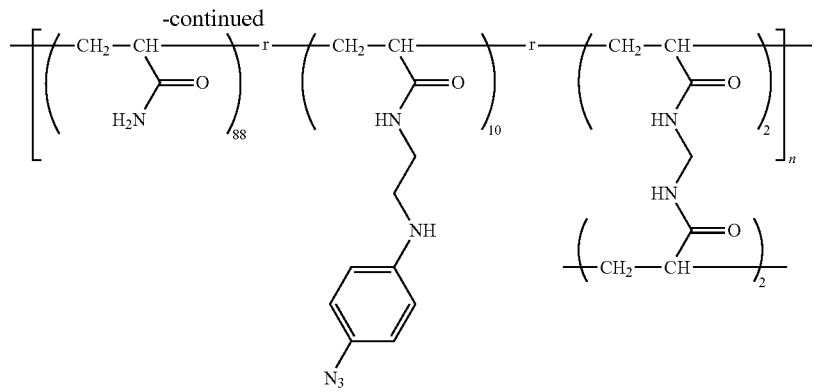

AAm (183 mg, 2.6 mmol), acrylic acid (AA) (20.6 μL, 0.3 mmol), MBAAm (19 mg, 0.12 mmol), and AIBN (2.5 mmol, 0.015 mmol) were dissolved in DMSO (1.5 mL), and subjected to argon bubbling for an hour, followed by reaction overnight at 70° C. to produce a gel. The gels were immersed in a DMSO solution in which N-(2-aminoethyl)-4-azidebenzamide (184 mg, 0.9 mmol), Bop reagent (39 mg, 0.9 mmol), and triethylamine (124 μL, 0.9 mmol) were dissolved, and reacted for 48 hours. The resulting gel was washed with DMSO, and immersed in water.

(1-3) Synthesis of Propargyl Group-Containing Hydrogel subjected to argon bubbling for an hour, followed by reaction overnight at 70° C. to produce a gel. The gels were immersed in a DMSO solution in which propargylamine (61 μL, 0.9 mmol), Bop reagent (39 mg, 0.9 mmol), and triethylamine (124 μL, 0.9 mmol) were dissolved, and reacted for 48 hours. The resulting gel was washed with DMSO, and immersed in water.

(2) Joining (Azide-Alkyne Cycloaddition Reaction)

Each gel obtained in (1-2) and (1-3) above was cut to a size of 4 mm×3 mm×2 mm, and the 4 mm×3 mm plane was used as the contact surface. The two gels were brought

[Chem. 26]

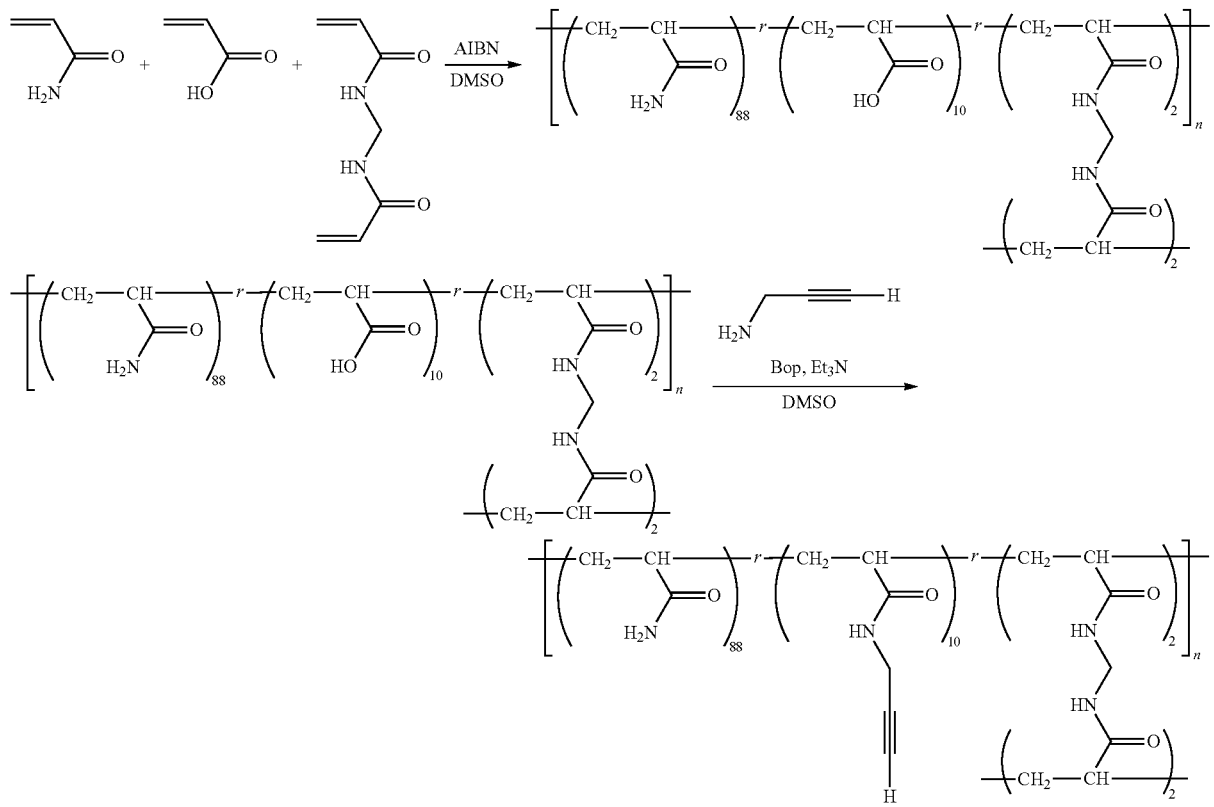

AAm (183 mg, 2.6 mmol), acrylic acid (AA) (20.6 μL, 0.3 mmol), MBAAm (19 mg, 0.12 mmol), and AIBN (2.5 mmol, 0.015 mmol) were dissolved in DMSO (1.5 mL), and together at their contact surfaces. After copper sulfate pentahydrate/sodium ascorbate=1/1.5 (mol/mol) suspended in water was added thereto, the gels were left unattended for eight hours. As a result, the gels were joined at their contact surfaces.

Comparative Example 4

The same procedures as in Example 2 (2) were performed, except that an acrylamide gel (a gel obtained by dissolving AAm (183 mg, 2.6 mmol), MBAAm (19 mg, 0.12 mmol), and APS (ammonium persulfate (ammonium peroxodisulfate), 2.5 mmol, 0.015 mmol) in water (1.5 mL), followed by argon bubbling for an hour and reaction for 70° C. overnight) was used instead of the azide group-containing hydrogel in (1-2). However, the gels were not joined.

Comparative Example 5

The same procedures as in Example 2 (2) were performed, except that an acrylamide gel (a gel obtained by dissolving AAm (183 mg, 2.6 mmol), MBAAm (19 mg, 0.12 mmol), and APS (ammonium persulfate (ammonium peroxodisulfate), 2.5 mmol, 0.015 mmol) in water (1.5 mL), followed by argon bubbling for an hour and reaction for 70° C. overnight) was used instead of the propargyl group-containing hydrogel in (1-3). However, the gels were not joined.

Comparative Example 6

In the procedures of Example 2 (2), the gels were left unattended for eight hours without adding sodium ascorbate. As a result, the gels were not joined.

Comparative Example 7

In the procedures of Example 2 (2), the gels were left unattended for eight hours without adding copper sulfate pentahydrate. As a result, the gels were not joined.

Example 3 (Solid-State Material: Gel and Glass Substrate, Covalent Bond: Carbon-Carbon Bond)

Figure 16:
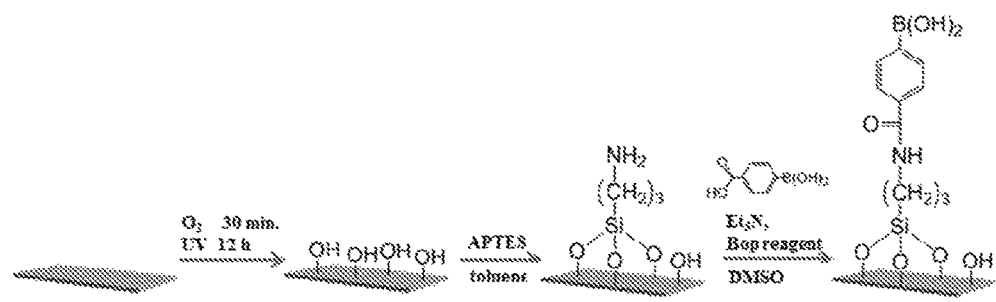
FIG. 16 is a synthetic scheme for the production of a boronic acid-containing glass substrate.

(1) Production of Boronic Acid-Containing Glass Substrate
A synthetic scheme is shown in FIG. 16.
A 50 mM 3-aminopropyltriethoxysilane-toluene solution (70 mL) was added to an ozone-treated 25 mm×50 mm glass substrate, followed by stirring for 24 hours. After washing it with toluene three times, a DMSO solution (70 mL) containing 4-carboxyphenyl boronic acid (250 mg, 1.5 mmol), triethylamine (0.30 mL, 2.1 mmol), and Bop reagent (930 mg, 2.1 mmol) was added and stirred for 24 hours. The resulting surface-modified glass substrate was washed with DMSO three times, and washed with water three times. A contact angle measurement (DCA-700 Dynamic Contact Angle Analyzer (Kyowa Interface Science Co., Ltd.)) revealed that the contact angle increased after the reaction. This shows that the hydrophilic glass substrate was changed to hydrophobic, thus confirming modification of the functional group.
(2) Joining (Suzuki-Miyaura Coupling)
The substrate produced in (1) above was overlaid on the 3 mm×3 mm surface of the gel obtained in Example 1 (1-2) cut to a size of 3 mm×3 mm×2 mm. The lamination was immersed in a potassium carbonate aqueous solution (0.1 g/mL). After palladium acetate dissolved in acetone was added thereto, the lamination was left unattended for 24 hours. As a result, the substrate and the gel were joined at their contact surfaces.

Example 4 (Solid-State Material: Gel and Glass Substrate, Covalent Bond: Carbon-Carbon Bond)

Figure 17:
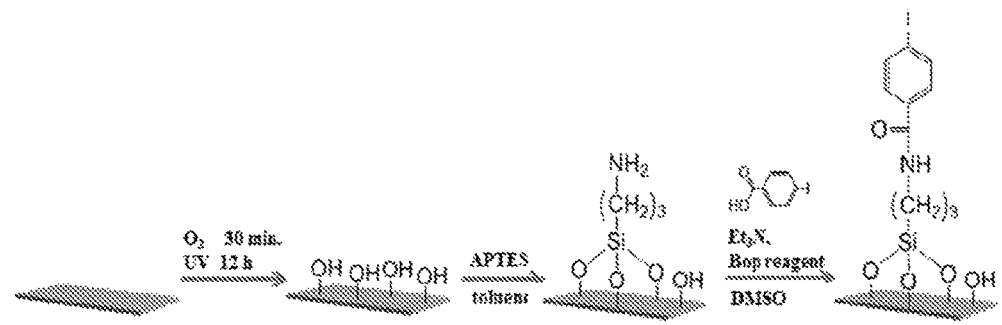
FIG. 17 is a synthetic scheme for the production of a halogenated aryl group-containing glass substrate.

(1) Halogenated Aryl Group-Containing Glass Substrate
A synthetic scheme is shown in FIG. 17.
A 50 mM 3-aminopropyltriethoxysilane-toluene solution (70 mL) was added to an ozone-treated 25 mm×50 mm glass substrate, followed by stirring for 24 hours. After washing with toluene three times, a DMSO solution (70 mL) containing 4-iodobenzoic acid (434 mg, 1.6 mmol), triethylamine (0.30 mL, 2.1 mmol), and Bop reagent (930 mg, 2.1 mmol) was added thereto and stirred for 24 hours. The resulting surface-modified glass substrate was washed with DMSO three times, and washed with water three times. A contact angle measurement (DCA-700 Dynamic Contact Angle Analyzer (Kyowa Interface Science Co., Ltd.)) revealed that the contact angle increased after the reaction. This shows that the hydrophilic glass substrate was changed to hydrophobic, thus confirming modification of the functional group.
(2) Joining (Suzuki-Miyaura Coupling)
The substrate produced in (1) above was overlaid on the 3 mm×3 mm surface of the gel obtained in Example 1 (1-1) cut to a size of 3 mm×3 mm×2 mm. The lamination was immersed in a potassium carbonate aqueous solution (0.1 g/mL). After palladium acetate dissolved in acetone was added thereto, the lamination was left unattended for 24 hours. As a result, the substrate and the gel were joined at their contact surfaces.

Example 5 (Solid-State Material: Gel and Glass Substrate, Covalent Bond: Carbon-Nitrogen Bond)

Figure 18:
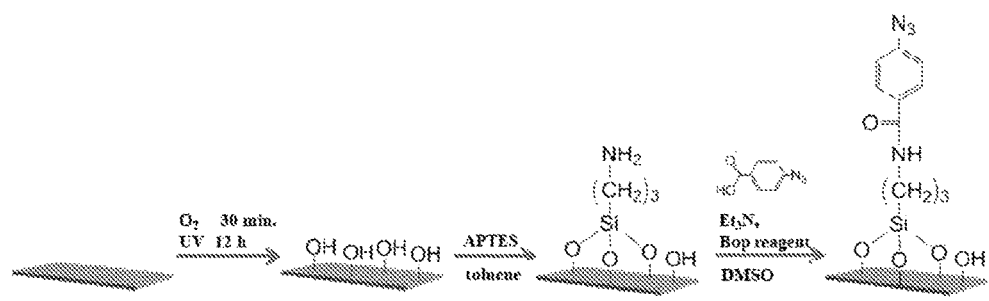
FIG. 18 is a synthetic scheme for the production of an azide group-containing glass substrate.

(1) Production of Azide Group-Containing Glass Substrate
A synthetic scheme is shown in FIG. 18.
A 50 mM 3-aminopropyltriethoxysilane-toluene solution (70 mL) was added to an ozone-treated 25 mm×50 mm glass substrate, followed by stirring for 24 hours. After washing with toluene three times, a DMSO solution (70 mL) containing 4-azidebenzoic acid (285 mg, 1.75 mmol), triethylamine (0.30 mL, 2.1 mmol), and Bop reagent (930 mg, 2.1 mmol) was added thereto and stirred for 24 hours. The resulting surface-modified glass substrate was washed with DMSO three times, and washed with water three times. A contact angle measurement (DCA-700 Dynamic Contact Angle Analyzer (Kyowa Interface Science Co., Ltd.)) revealed that the contact angle increased after the reaction. This shows that the hydrophilic glass substrate was changed to hydrophobic, thus confirming modification of the functional group.
(2) Joining (Azide-Alkyne Cycloaddition Reaction)
The substrate produced in (1) above was overlaid on the 3 mm×3 mm surface of the gel obtained in Example 1 (1-3) cut to a size of 3 mm×3 mm×2 mm. After copper sulfate pentahydrate/sodium ascorbate=1/1.5 (mol/mol) suspended in water was added thereto, the lamination was left unattended for 24 hours. As a result, the gel and the substrate were joined at their contact surfaces.

Example 6 (Solid-State Material: Gel, Covalent Bond: Amide Bond, Host-Guest Interaction)

Figure 19:
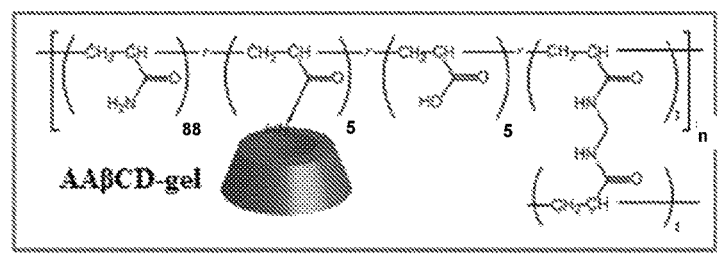
FIG. 19 is a structural depiction of a carboxy group- and host group-containing gel.

(1) Synthesis of Carboxy Group- and Host Group-Containing Gel
AAm (103 mg, 1.44 mmol), AA (5.7 µL, 0.08 mmol), 6-acrylamide-βCD (98 mg, 0.08 mmol), MBAAm (5.3 mg, 0.03 mmol), ammonium disulfate (APS) (20 mg, 0.09 mmol), and N,N,N',N'-tetramethyl ethylenediamine (TEMED) (12.4 μL) were dissolved in water (0.75 mL), and subjected to argon bubbling for an hour, followed by reaction overnight at room temperature, thereby obtaining a gel. The resulting gel was washed with water. A depiction of the gel appears in FIG. 19.

(2) Synthesis of Amino Group- and Guest Group-Containing Gel

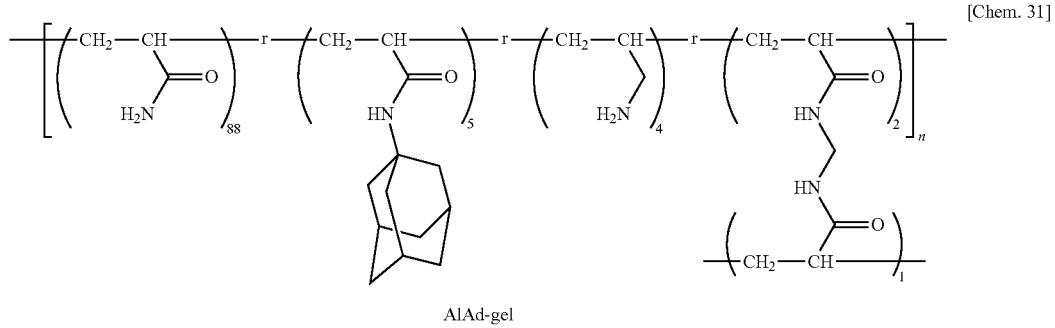

AlAd-gel

AAm (103 mg, 1.44 mmol), allylamine (12.5 μL, 0.08 mmol), 1-adamantane acrylamide (17.6 mg, 0.08 mmol), MBAAm (5.3 mg, 0.03 mmol), APS (20 mg, 0.09 mmol) and TEMED (12.4 μL) were dissolved in water (0.75 mL), and subjected to argon bubbling for an hour, followed by reaction overnight at room temperature, thereby obtaining a gel. The resulting gel was washed with water.

(3) Joining (Host-Guest Interaction and Amide Bond-Forming Reaction)

Each gel obtained in (1) and (2) above was cut to a size of 3 mm×3 mm×3 mm, and the gels were brought together in water. After 24 hours, 4-(4,6-dimethoxy-1,3,5-triazin-2-yl)-4-methylmorpholinium chloride (DMT-MM) was added, and the gels were left unattended for 48 hours. As a result, the gels were joined at their contact surfaces.

Reference Example 1 (Competitive Test)

The joined gels obtained in Example 6 were placed in water in the presence of DMT-MM. After adamantane amine hydrochloride was added, the gels were left unattended for a day. Dissociation of the gels was not observed.

Test Example 3 (Evaluation of Joining Strength)

Figure 4:
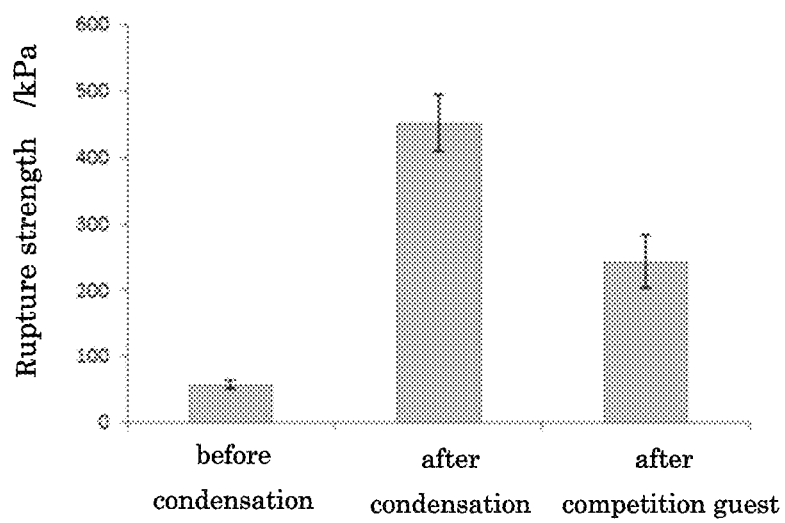
FIG. 4 is a graph showing rupture stress, according to Test Example 3.

The rupture stresses of the gels before addition of DMT-MM and the gels left unattended for 48 hours after addition of DMT-MM in Example 6 (3), and the gels left unattended for a day after addition of adamantane amine hydrochloride in Reference Example 1 were measured. FIG. 4 shows the results.

Joined Body Joined by Coordinate Bond

Example 7

Figure 20:
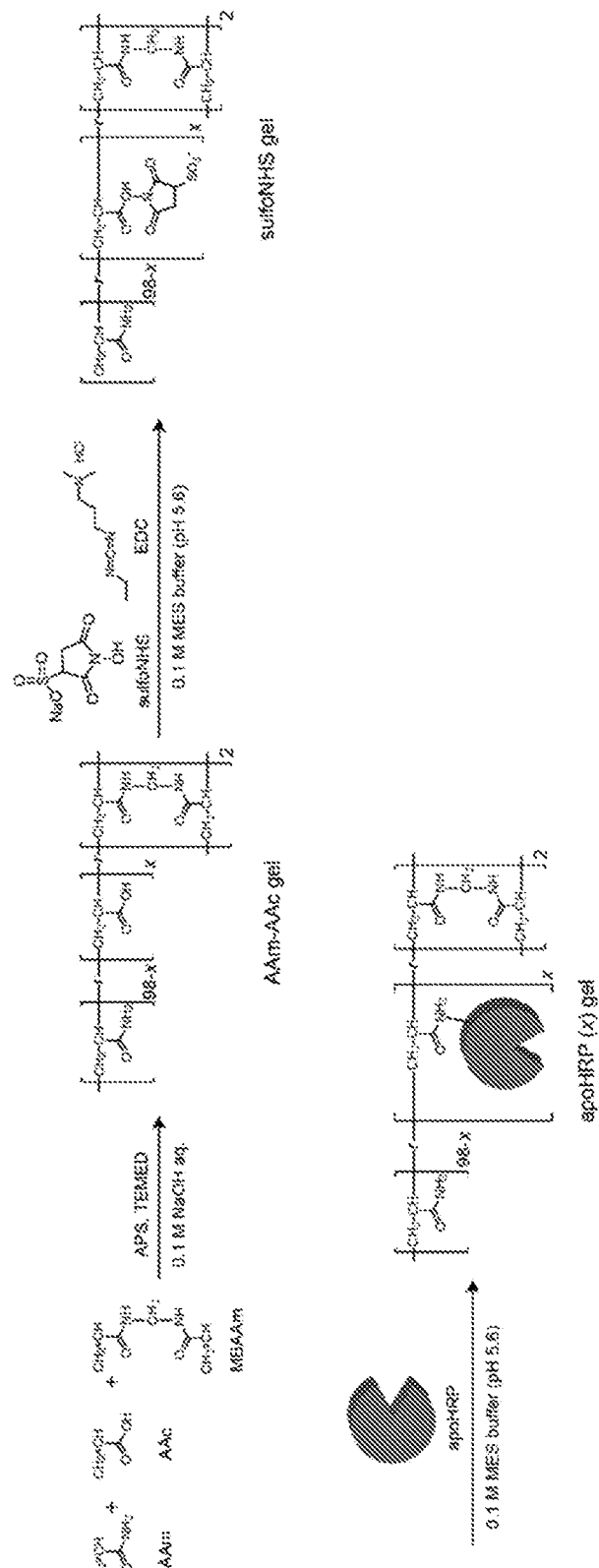
FIG. 20 is a synthetic scheme for the production of a gel modified with apohorseradish peroxidase (apHRP).

(1) Synthesis of Gel
(1-1) Synthesis of Gel Modified with Apohorseradish Peroxidase (apHRP)
A synthetic scheme appears in FIG. 20

(1-1-1) Synthesis of AAm-AAc Gel

Acrylamide (AAm) (0.29 g, 4.1 mmol), acrylic acid (AAc) (3.0 mg, 42 μmol) and N,N'-methylene-bis-acrylamide (MBAAm) (13 mg, 83 μmol) were dissolved in 0.1 M sodium hydroxide aqueous solution (NaOH aq.) (2.0 mL). Ammonium peroxodisulfate (APS) (19 mg, 83 μmol) and N,N,N',N'-tetramethyl-1,2-ethanediamine (TEMED) (12 μL, 83 μmol) were added to the solution, and left unattended for an hour at room temperature, thereby obtaining a gel. The resulting gel was washed with a large amount of water, thereby removing the monomer and the initiator. Thereafter, the gel was immersed in 0.1 M 2-morpholino ethane sulfonic acid buffer solution (MES buffer) (pH 5.6).

(1-1-2) Synthesis of SulfoNHS Gel

AAm-AAc gel was immersed in a 0.1 M MES buffer (pH 5.6) mixed solution containing 10 mM 1-ethyl-3-(3-dimethylaminopropyl)carbodiimide hydrochloride (EDC) and 20 mM 1-hydroxy-2,5-dioxopyrrolidine-3-sulfonic acid sodium salt (sulfoNHS) for 10 hours at room temperature. The resulting gel was washed with a large amount of 0.1 M MES buffer (pH 5.6).

(1-1-3) Synthesis of apoHRP (x)

The sulfoNHS gel was immersed in a 374 μM apohorseradish peroxidase aqueous solution (10 mL) for 14 hours at room temperature. The resulting gel was washed with a 0.1 M MES buffer (pH 5.6), and then immersed in a buffer (50 mM sodium phosphate buffer solution containing 4 wt % of DMSO (pH 7.0)). An apohorseradish peroxidase-modified gel having an acrylic acid-derived unit of 0.8 mol % (33 μmol) was obtained.

The acrylic acid-derived unit was calculated by performing ultraviolet-visible-near-infrared (UV-Vis) spectrophotometry directly with respect to the obtained gel (film thickness=50 μm) and based on the absorbency at 278 nm of apoHRP in the solution according to Lambert-Beer Formula (A) below.

[Math. 1]

$$A_{278\ nm} = \varepsilon_{278\ nm} \times C \times l_{apoHRP\ gel} \quad (A)$$

$A_{278\ nm}$; 1.4
$\varepsilon_{278\ nm}$; $2.0 \times 10^4$ mol$^{-1}$Lcm$^{-1}$
$l_{apoHRP\ gel}$ (Thickness of apoHRP gel); 50 μm
C (Concentration of apoHRP in gel); 15.2 mM
x in apoHRP(x)gel; 0.80 mol %

(1-2) Synthesis of Iron Porphyrin-Modified Gel

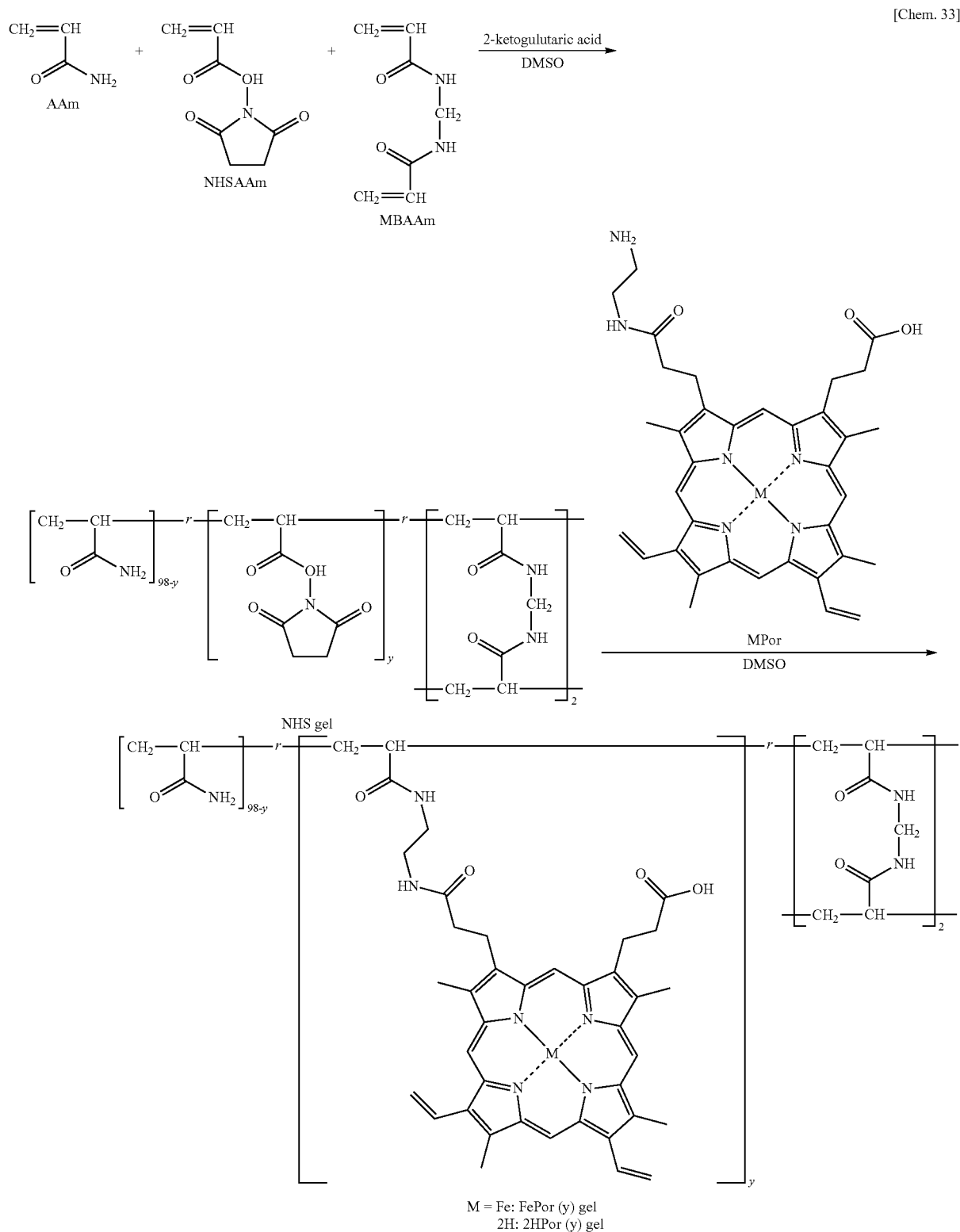

M = Fe: FePor (y) gel
2H: 2HPor (y) gel (1-2-1) Synthesis of NHS Gel

AAm (0.27 g, 3.9 mmol), MBAAm (12 g, 0.08 mmol) and N-succinimidyl acrylate (NHS-AAm) (30 mg, 0.12 mmol) were dissolved in dimethyl sulfoxide (DMSO) (2.0 mL), followed by argon gas bubbling for 3 hours. After 2-ketoglutaric acid (3.0 mg, 21 µmol) was added, the solution was left unattended at 60° C. for eight hours, thereby obtaining a gel.

(1-2-2) Synthesis of FePor Gel

The NHS gel was immersed in DMSO in which iron porphyrin (FePor) was dissolved. The resulting gel was washed with a large amount of DMSO, and immersed in a buffer. An iron porphyrin-modified gel having an NHS-AAm-derived unit of 1.0 mol % (0.041 mmol) was obtained. The NHS-AAm derived unit was calculated as follows, in a manner similar to that in (1-1-3) above.
[Math. 2]

$$A_{410\ nm} = \varepsilon_{410\ nm} \times C \times l_{FePor\ gel} \quad (B)$$

$A_{410\ nm}$; 1.8
$\varepsilon_{410\ nm}$; $9.0 \times 10^4$ mol$^{-1}$Lcm$^{-1}$
$l_{FePor\ gel}$; 10 μm
C (Concentration of FePor in gel); 20 mM
y in FePor(y)gel; 1.0 mol %
(2) Joining (Coordinate Bond)

Each gel obtained in (1-1) and (1-2) above was cut to a size of 5 mm×5 mm×2 mm, and the 5 mm×5 mm plane was used as the contact surface. The two gels were brought together at their contact surfaces, and left unattended for 45 minutes at 4° C. As a result, the gels were joined at their contact surfaces.

Comparative Example 8

In the procedures of Example 7 (2), the gels obtained in (1-1) were used. As a result, the gels were not joined.

Comparative Example 9

In the procedures of Example 7 (2), the gels obtained in (1-2) were used. As a result, the gels were not joined.

Comparative Example 10

(1) Synthesis of Blank Gel

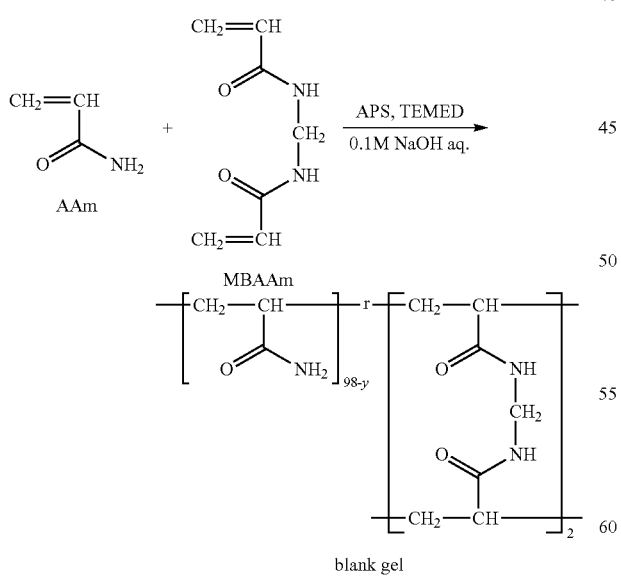

blank gel

AAm (0.29 g, 4.1 mmol) and MBAAm (13 mg, 83 μmol) were dissolved in 0.1 M NaOH aqueous solution (2.0 mL). APS (19 mg, 83 μmol) and TEMED (12 μL, 83 μmol) were added thereto, thereby obtaining a gel. The resulting gel was washed with a large amount of water, thereby removing the monomer and the initiator. Thereafter, the gel was immersed in a buffer.
(2) Joining The same procedures as in Example 7 (2) were performed, except that the gels obtained in (1) above were used instead of the gels modified with apohorseradish peroxidase in (1-1). As a result, the gels were not joined.

Comparative Example 11

The same procedures as in Example 7 (2) were performed, except that the gels obtained in Comparative Example 10 (1) above were used instead of the gels modified with iron porphyrin in (1-2). As a result, the gels were not joined.

Comparative Example 12

(1) Synthesis of Gel Modified with Porphyrin in which Iron is not Introduced

A gel was synthesized in the same manner as in Example 7 (1-2-2), except that porphyrin (2HPor) without iron coordination was used instead of iron porphyrin (FePor). The identification was performed as follows, in a manner similar to that in Example 7.
[Math. 3]

$$A_{383\ nm} = \varepsilon_{383\ nm} \times C \times l_{2HPor\ gel} \quad (C)$$

$A_{383\ nm}$; 2.8
$\varepsilon_{383\ nm}$; $1.4 \times 10^5$ mol$^{-1}$Lcm$^{-1}$
$l_{2HPor\ gel}$; 10 μm
C (Concentration of 2HPOr in gel); 20 mM
y in 2HPor(y)gel; 1.0 mol %
(2) Joining The same procedures as in Example 7 (2) were performed, except that the gels obtained in (1) above in which iron was not introduced were used instead of the gels modified with iron porphyrin in (1-2). As a result, the gels were not joined.

Reference Example 2 (Competitive Test)

The joined gels obtained in Example 7 were shaken in a buffer at 4° C. for 20 minutes. Dissociation of the gels was not observed. The buffer was removed, 350 μM apoHRP buffer solution was added, and the gels was shaken at 4° C. for 20 minutes. As a result, the gels were dissociated from the joining portion.

Test Example 4 (Evaluation of Catalytic Activity)

Figure 5:
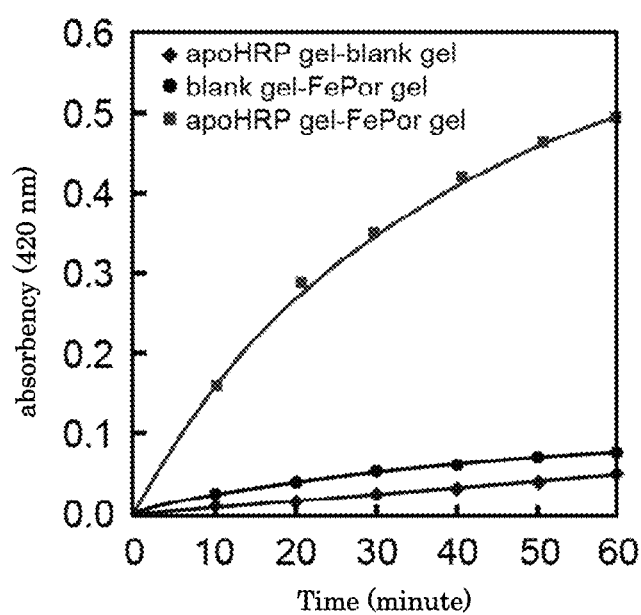
FIG. 5 is a graph showing a change in absorbency at 420 nm, according to Test Example 4.

The gels (5 mm×5 mm×2 mm) obtained in Example 7 (1-1) and (1-2) were placed in a buffer solution in which 5 mM $H_2O_2$ and 2.0 mM pyrogallol were dissolved. A 5 g weight was placed thereon to closely attach the gels. At the time, the change in absorbency at 420 nm for tracking the oxidation of pyrogallol was measured. FIG. 5 shows the results.

Test Example 5 (Change in Catalytic Activity Due to Change in Amounts of Apoenzyme and Cofactor)

(1) The same procedures as in Example 7 (1-2) were performed, except that the amount of NHS-AAm was changed to 10 mg (0.04 mmol), thereby obtaining an iron porphyrin-modified gel having an NHS-AAm-derived unit of 0.47 mmol.

(2) The same procedures as in Example 7 (1-1) were performed, except that a 35 µM apohorseradish peroxidase aqueous solution was used, thereby obtaining an apohorseradish peroxidase-modified gel having an acrylic acid-derived unit of 0.22 mol % (9.1 µmol).

Figure 6:
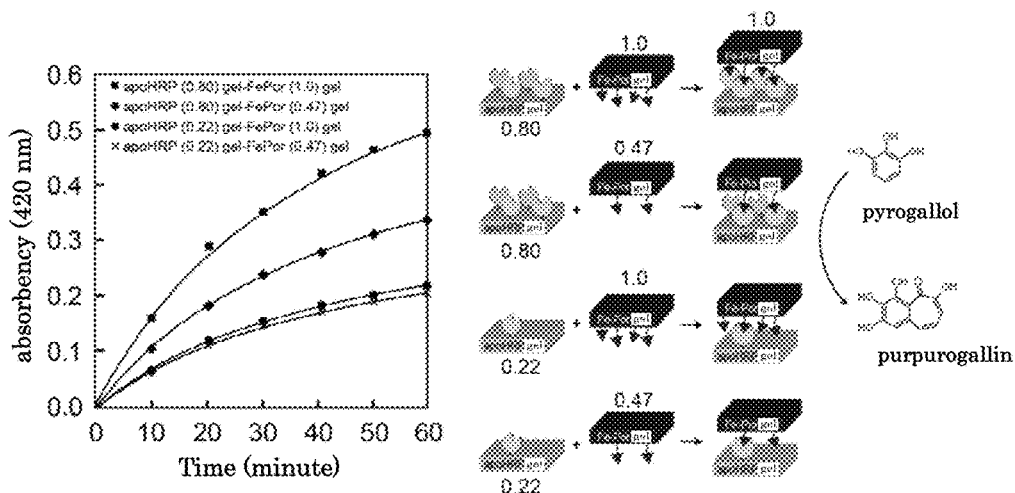
FIG. 6 is a graph showing a change in absorbency at 420 nm, according to Test Example 5.

(3) A test similar to that of Test Example 4 was performed with respect to a combination of the gel obtained in Example 7 (1-1) and the gel obtained in (1) above, a combination of the gel obtained in Example 7 (1-2) and the gel obtained in (2) above, and a combination of the gel obtained in (1) above and the gel obtained in (2) above, instead of the gels obtained in Example 7 (1-1) and (1-2). FIG. 6 shows the results, together with the results of Test Example 4.

Test Example 6 (Evaluation of Catalytic Activity in Air)

The gel obtained in Example 7 (1-1) was immersed in a buffer solution in which 0.5 mM ABTS and 5.0 mM $H_2O_2$ were dissolved for a day. The gel was removed from the buffer solution, and its surface was washed with a buffer (5 mm×5 mm×2 mm). Thereafter, the gel obtained in Example 7 (1-2) was overlaid on the gel, and a 5 g weight was placed thereon. The gels were left unattended at room temperature. As a result, only the contact surfaces of the gels turned blue, which is a color derived from a peroxide of ABTS.

Test Example 7 (Control of Catalytic Activity by Joining-Dissociation)

The gels obtained in Example 7 (1-1) and (1-2) were brought together in a buffer solution in which 2.0 mM pyrogallol and 5.0 mM $H_2O_2$ were dissolved. A 5 g weight was placed on the gels, and pyrogallol oxidation reaction was performed. Steps (a) and (b) below were repeated every two minutes.

(a) The weight was removed with tweezers, and FePor was dissociated directly by hand.

(b) FePor was placed on apoHRP, and a weight (5 g) was placed thereon, thereby joining the gels.

Figure 7:
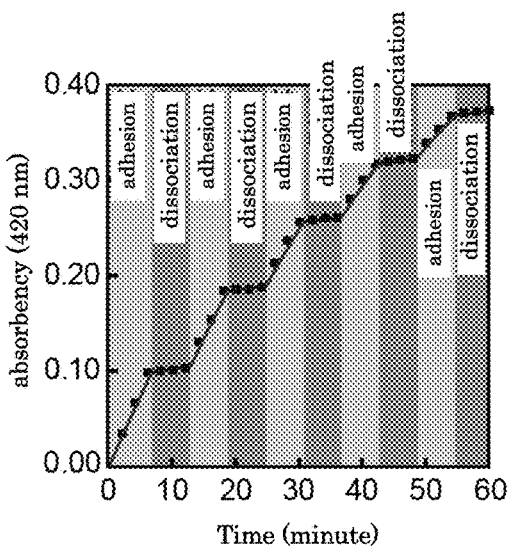
FIG. 7 is a graph showing a change in joining-dissociation, according to Test Example 7.

FIG. 7 shows the results.

Joined Body Joined by Hydrogen Bond

Example 8

(1) Synthesis of Gel
(1-1-1) Synthesis of Adenine-Containing Monomer

[Chem. 35]

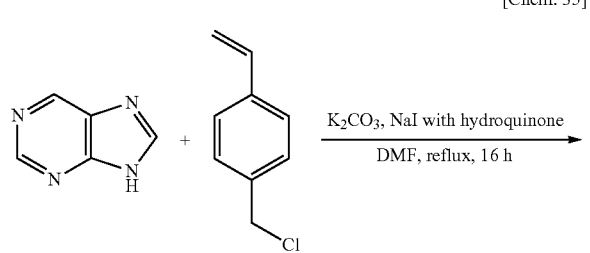

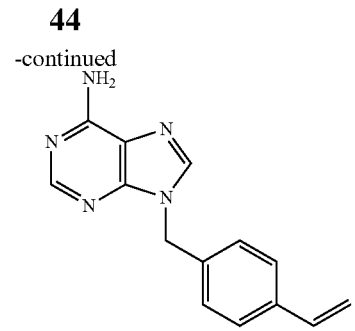

Figure 8:
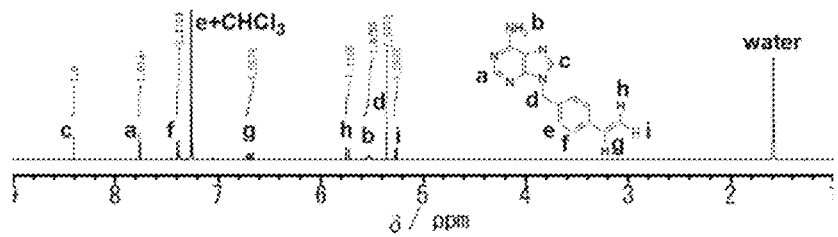
FIG. 8 is $^1$H-NMR data of a monomer obtained in (1-1-1) of Example 8.

Adenine (3.4 g, 25 mmol), potassium carbonate (3.8 g, 27 mmol), sodium iodide (45 mg, 0.3 mmol) and hydroquinone (5.0 mg, 0.05 mmol) were suspended in 50 ml of N,N-dimethylformamide (DMF) under argon atmosphere. 4-chloromethylstyrene (3.6 ml, 25 mmol) was added thereto, and the mixture was heated at 160° C. under reflux overnight. The mixture was subjected to hot filtration, and washed with DMF 2×25 ml. The filtrate was concentrated and dried to hardness, and 15 g of silica gel and chloroform 2×50 ml of were added, followed by filtration thereby collecting a filtrate. The collected filtrate was concentrated and purified by silica gel column chromatography (chloroform:methanol=95:5, Rf=0.24), thereby obtaining 0.49 g of a white solid (yield=8%). FIG. 8 shows $^1$H-NMR data.

(1-1-2) Synthesis of Adenine-Containing Gel

[Chem. 36]

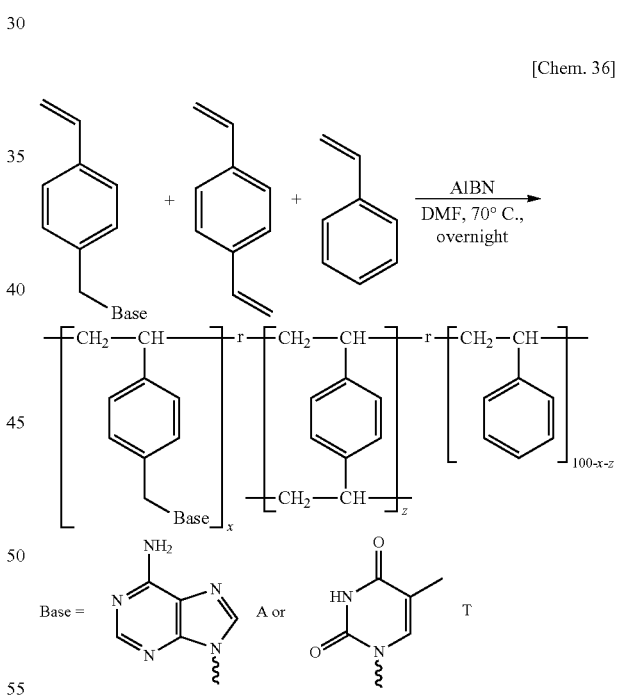

5 mol % (25.1 mg) of the adenine-containing monomer obtained in (1-1-1), 10 mol % (28.5 µL) of divinylbenzene, 85 mol % (195.4 µL) of styrene, and 1 mol % (3.3 mg) of azobisisobutyronitrile (AIBN) were mixed and dissolved in DMF (1 mL) so that the total monomer concentration became 2 M. The resulting solution was subjected to argon bubbling for an hour, and heated to 70° C. in an oil bath for polymerization. The resulting gel was subjected to solvent substitution by being repeatedly washed with toluene, thereby obtaining a gel.

(1-2-1) Synthesis of Thymine-Containing Monomer

[Chem. 37]

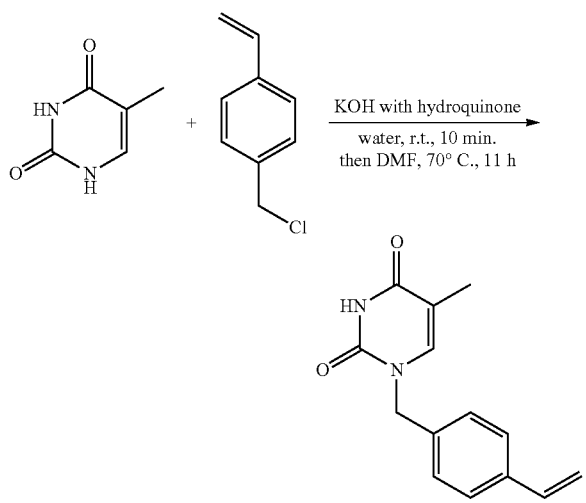

Figure 9:
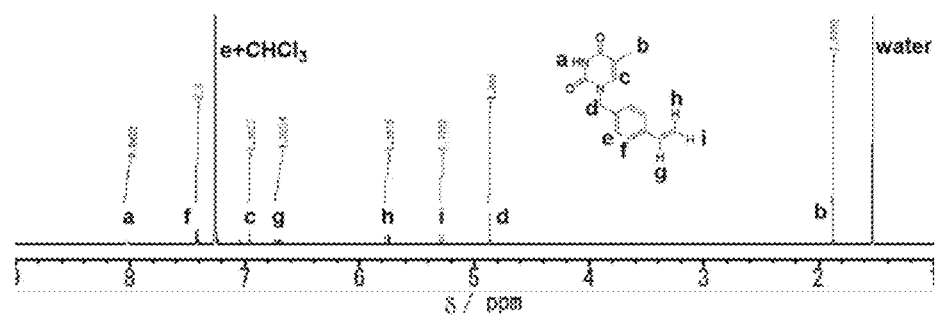
FIG. 9 is $^1$H-NMR data of a monomer obtained in (1-2-1) of Example 8.

Thymine (1.2 g, 10 mmol) and 0.63 g of potassium hydroxide (11 mmol) were evenly dissolved in water, and freeze-dried. 5.0 mg (0.05 mmol) of hydroquinone was added thereto, and 260 ml of DMF and 4-chloromethylstyrene (1.4 ml, 10 mmol) were added under argon atmosphere, and the mixture was stirred at 70° C. for 11 hours. The solvent was distilled off, followed by recrystallization with toluene, thereby obtaining 0.51 g of a white solid (yield=22%). FIG. 9 shows $^1$H-NMR data.

(1-2-2) Synthesis of Thymine-Containing Gel 5 mol % (24.2 mg) of the thymine-containing monomer obtained in (1-2-1), 10 mol % (28.5 μL) of divinylbenzene, 85 mol % (195.4 μL) of styrene, and 1 mol % (3.3 mg) of azobisisobutyronitrile (AIBN) were mixed and dissolved in DMF (1 mL) so that the total monomer concentration became 2 M. The resulting solution was subjected to argon bubbling for an hour, and heated to 70° C. in an oil bath for polymerization. The resulting gel was subjected to solvent substitution by being repeatedly washed with toluene, thereby obtaining a gel.

(2) Joining (Hydrogen Bond)

Each gel obtained in (1-1-2) and (1-2-2) was cut to a size of 3 mm×3 mm×3 mm, and was shaken in toluene (3 mL). As a result, the gels were joined.

Example 9

(1) Synthesis of Gel
(1-1) Synthesis of Oligonucleotide Monomer

Oligonucleotides having the following oligonucleotide sequences (1-1-1') and (1-1-2') from 3' end were synthesized using a commercially available DNA synthesizer and a phosphoroamidite method.

```
(1-1-1'):
5'-TTTTTCACAGATGAGT-3'

(1-1-2'):
5'-TTTTACTCATCTGTGA-3'
```

The compound (Acr) represented by Formula (23) below was reacted with each 5' end of the sequences, thereby synthesizing oligonucleotide monomers (1-1-1) and (1-1-2) having a double bond at the 5' end, as shown in [Chem. 39] below (a part of the nucleotide is omitted).

[Chem. 38]

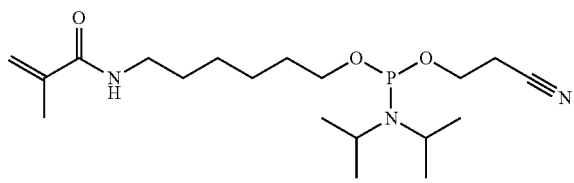

(23)

[Chem. 39]

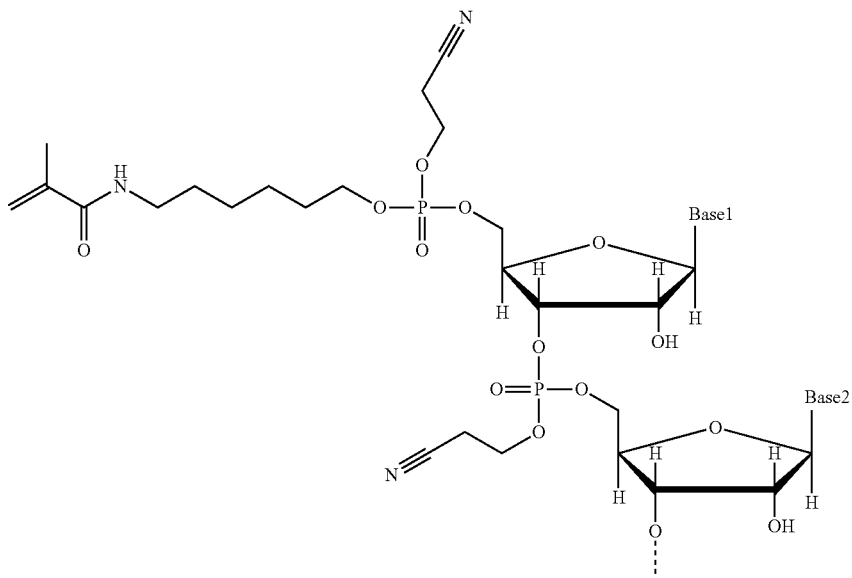

(1-1-1):
5'-Acr-TTTTTCACAGATGAGT-3'
(1-1-2):
5'-Acr-TTTTACTCATCTGTGA-3'

(1-2) Synthesis of Oligonucleotide-Containing Gel

AAm (69.7 mg, 0.98 mmol), an oligonucleotide monomer (20 nmol) having the sequence (1-1-1) above, MBAAm (0.8 mg, 0.005 mmol), ammonium peroxodisulfate (APS) (2.3 mg, 0.01 mmol), and N,N,N',N'-tetramethyl ethylenediamine (TEMED) (1.5 µL, 0.01 mmol) were dissolved in water (1 mL), and reacted overnight at room temperature, thereby obtaining a gel. The resulting gel was washed with water.

In a similar manner, a gel was obtained using an oligonucleotide monomer having the sequence (1-1-2).

(2) Joining (Hydrogen Bond)

Each of the gels having sequences (1-1-1) and (1-1-2) above was cut to a size of 5 mm×5 mm×5 mm, and the gels were brought into direct contact with each other and left unattended overnight in a refrigerator. As a result, the gels were joined at their contact surfaces.

Comparative Example 13

(1) Synthesis of Gel

A gel having a sequence 5'-Acr-TTTTTTTTTTTTTTTT-3'(1-1-3) was produced in a manner similar to that of Example 9 (1).

(2) Joining (Hydrogen Bond)

The same procedures as in Example 9 (2) were performed, except that a combination of gels having sequences (1-1-1) and (1-1-3) above, and a combination of gels having sequences (1-1-2) and (1-1-3) above were used. As a result, the gels were not joined.

Test Example 8

Figure 10:
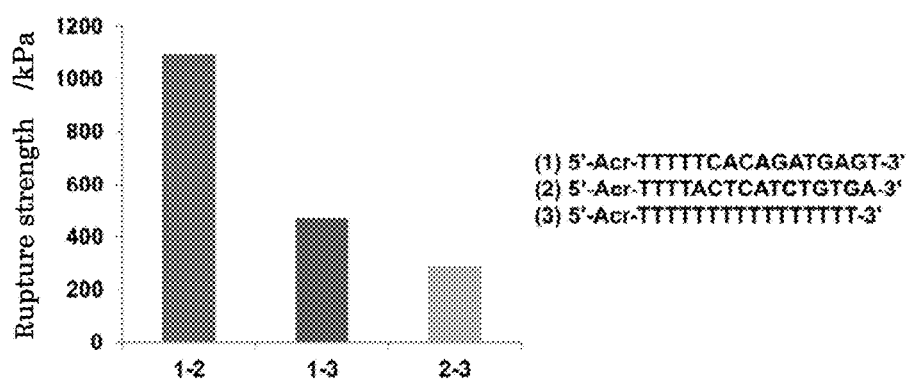
FIG. 10 is a graph showing rupture strength, according to Test Example 8.
Figure 11:
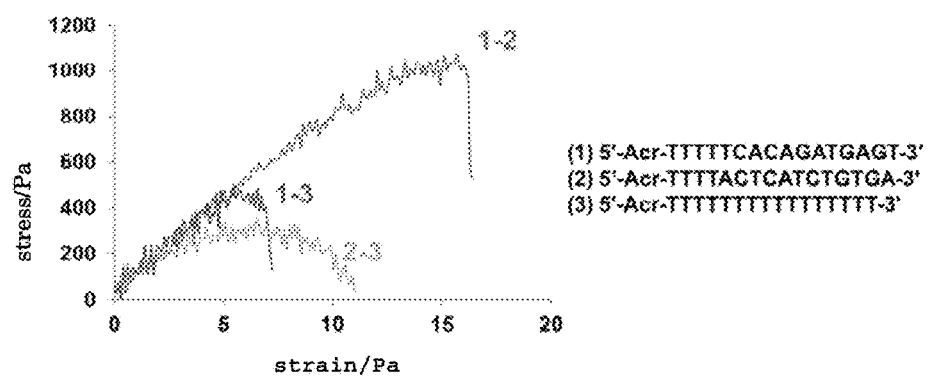
FIG. 11 is a graph representing a stress-strain curve, according to Test Example 8.

Each gel obtained in Example 9 and Comparative Example 10 having been subjected to solvent substitution with Tris/HCl buffer (pH 8) in which 50 mM NaCl and 10 mM $MgCl_2$ were dissolved was cut to a size of 8 mm×4 mm×2 mm. The gels were brought into contact at their 4 mm×2 mm surfaces in a combination of (1-1-1) and (1-1-2), (1-1-1) and (1-1-3), and (1-1-2) and (1-1-3). A tensile test was performed three times for each combination. FIGS. 10 and 11 show the results of rupture strength and stress-strain curves, respectively.

INDUSTRIAL APPLICABILITY

The joined body of the present invention ensures stable and strong joining when the chemical bond is a covalent bond.

Further, in the joined body of the present invention, when the chemical bond is a coordinate bond (in particular, apoenzyme-cofactor interaction), a catalytic activity may be added to the joined body. Furthermore, since the catalytic activity can be artificially controlled, the present invention is expected to be applied to therapeutic agents, experimental enzymatic reactions, and the like.

Additionally, the present invention ensures selective and significantly precise joining when the chemical bond is a hydrogen bond (in particular, complementary interaction between nucleic acid bases). Further, the joined body produced by using complementary interaction between nucleic acid bases may be applied to DNA sequence recognition.

The invention claimed is:

1. A joined body, wherein two or more same or different solid-state materials are joined directly by a chemical bond at their contact interfaces,
wherein the solid-state materials are:
a solid-state material containing a boronic acid group and a solid-state material containing an aryl halide group;
a solid-state material containing an azide group and a solid-state material containing an ethynyl group; or
a solid-state material containing a carboxy group and a solid-state material containing an amino group.

2. A joined body, wherein two or more same or different solid-state materials are joined directly by a chemical bond at their contact interfaces,
wherein the chemical bond is a coordinate bond,
wherein a gel containing an apoenzyme and a gel containing a cofactor are used as the solid-state materials.

3. A joined body, wherein two or more same or different solid-state materials are joined directly by a chemical bond at their contact interfaces, wherein the chemical bond is a hydrogen bond, and
wherein a gel containing a first nucleic acid base and a gel containing a second nucleic acid base complementary to the first nucleic acid base are used as the solid-state materials.

4. A joined body, wherein two or more same or different solid-state materials are joined directly by a chemical bond at their contact interfaces, wherein the chemical bond is a hydrogen bond, and
wherein the solid-state materials are gels containing an oligonucleotide.

5. A method for producing a joined body by reacting a solid-state material containing a boronic acid group and a solid-state material containing an aryl halide group at their contact interfaces in the presence of a catalyst.

6. A method for producing a joined body by reacting a solid-state material containing an azide group and a solid-state material containing an ethynyl group at their contact interfaces in the presence of a catalyst.

7. A method for producing a joined body by reacting a solid-state material containing a carboxy group and a solid-state material containing an amino group at their contact interfaces in the presence of a catalyst, wherein the solid-state material is at least one kind selected from gels, glass, wooden plates, plastic, metal plates, and paper.

* * * * *

SEQUENCE LISTING

```
<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide descriped in example
      9 as 1-1-1'

<400> SEQUENCE: 1
tttttcacag atgagt                                                     16

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide descriped in example
      9 as 1-1-2'

<400> SEQUENCE: 2
ttttactcat ctgtga                                                     16

<210> SEQ ID NO 3
<211> LENGTH: 16
<212> TYPE: DNA
<213> ORGANISM: Artificial Sequence
<220> FEATURE:
<223> OTHER INFORMATION: synthetic oligonucleotide descriped in example
      9 as 1-1-1
```

```
<220> FEATURE:
<221> NAME/KEY: misc_feature
<222> LOCATION: (1)..(1)
<223> OTHER INFORMATION: modified with Acr, which is described in
      specification as chemical formula 23

<400> SEQUENCE: 3
tttttcacag atgagt                                                     16

<210> SEQ ID NO 4
<211> LENGTH: 16
<212> TYPE: DNA
<213> ORGANISM: Artificial Sequence
<220> FEATURE:
<223> OTHER INFORMATION: synthetic oligonucleotide descriped in example
      9 as 1-1-2
<220> FEATURE:
<221> NAME/KEY: misc_feature
<222> LOCATION: (1)..(1)
<223> OTHER INFORMATION: modified with Acr, which is described in
      specification as chemical formula 23

<400> SEQUENCE: 4
ttttactcat ctgtga                                                     16

<210> SEQ ID NO 5
<211> LENGTH: 16
<212> TYPE: DNA
<213> ORGANISM: Artificial Sequence
<220> FEATURE:
<223> OTHER INFORMATION: synthetic oligonucleotide descriped in
      comparative example 13 as 1-1-3
<220> FEATURE:
<221> NAME/KEY: misc_feature
<222> LOCATION: (1)..(1)
<223> OTHER INFORMATION: modified with Acr, which is described in
      specification as chemical formula 23

<400> SEQUENCE: 5
tttttttttt tttttt                                                     16
```